US009498572B2

(12) United States Patent
Bally

(10) Patent No.: US 9,498,572 B2
(45) Date of Patent: Nov. 22, 2016

(54) DOUBLE ARM POST SUPPORT ASSEMBLY

(71) Applicant: Nexxspan Healthcare, LLC, Lithia, FL (US)

(72) Inventor: Alexander Bally, Marston Mills, MA (US)

(73) Assignee: Nexxspan Healthcare, LLC, Lithia, FL (US)

( * ) Notice: Subject to any disclaimer, the term of this patent is extended or adjusted under 35 U.S.C. 154(b) by 0 days.

(21) Appl. No.: 14/713,353

(22) Filed: May 15, 2015

(65) Prior Publication Data

US 2015/0328397 A1   Nov. 19, 2015

Related U.S. Application Data

(60) Provisional application No. 61/993,555, filed on May 15, 2014.

(51) Int. Cl.

| A61M 5/14 | (2006.01) |
|---|---|
| F16M 13/02 | (2006.01) |
| A47F 5/04 | (2006.01) |
| A47F 5/05 | (2006.01) |
| A47F 5/06 | (2006.01) |
| A47B 46/00 | (2006.01) |

(52) U.S. Cl.
CPC .............. *A61M 5/1415* (2013.01); *A47F 5/04* (2013.01); *A47F 5/05* (2013.01); *A47F 5/06* (2013.01); *F16M 13/022* (2013.01); *A47B 46/005* (2013.01); *F16M 2200/065* (2013.01); *Y10T 29/49842* (2015.01)

(58) Field of Classification Search
CPC ................ F16M 11/06; F16M 11/2014; A47F 5/04;A47F 5/05; A47F 5/06; A47F 5/106; A47B 45/005; A47B 43/00; A47G 25/0664; D06F 57/04; D06F 57/08
USPC ........................... 248/647, 276.1; 211/85.13
See application file for complete search history.

(56) References Cited

U.S. PATENT DOCUMENTS

| 2,232,952 A | 2/1941 | Longfellow |
| 2,658,507 A | 11/1953 | Neufeld |
| 3,390,897 A | 7/1968 | Moore |
| 5,379,205 A | 1/1995 | Peng |
| 2009/0314923 A1 | 12/2009 | Timoszyk et al. |

OTHER PUBLICATIONS

Bally, Alexander; PCT Application entitled: Double Arm Post Support Assembly having serial No. PCT/US15/30994, filed May 15, 2015, 45 pgs.
Bally, Alexander; U.S. Provisional Application Entitled: Double Arm Post Support Assembly, U.S. Appl. No. 61/993,555, filed May 15, 2014, 9 pgs.
Bally, Alexander; International Search Report and Written Opinion for Application No. PCT/US15/30994, filed May 15, 2015, mailed Aug. 17, 2015, 9 pgs.

*Primary Examiner* — Brian Glessner
*Assistant Examiner* — Paola Agudelo
(74) *Attorney, Agent, or Firm* — Taylor English Duma LLP

(57) ABSTRACT

A support arm assembly includes a support arm, the support arm including a support arm connector hub and a support arm body; and a split arm, the split arm including a split arm connector hub and a support hub, the split arm connector hub connecting to the support arm connector hub.

25 Claims, 13 Drawing Sheets

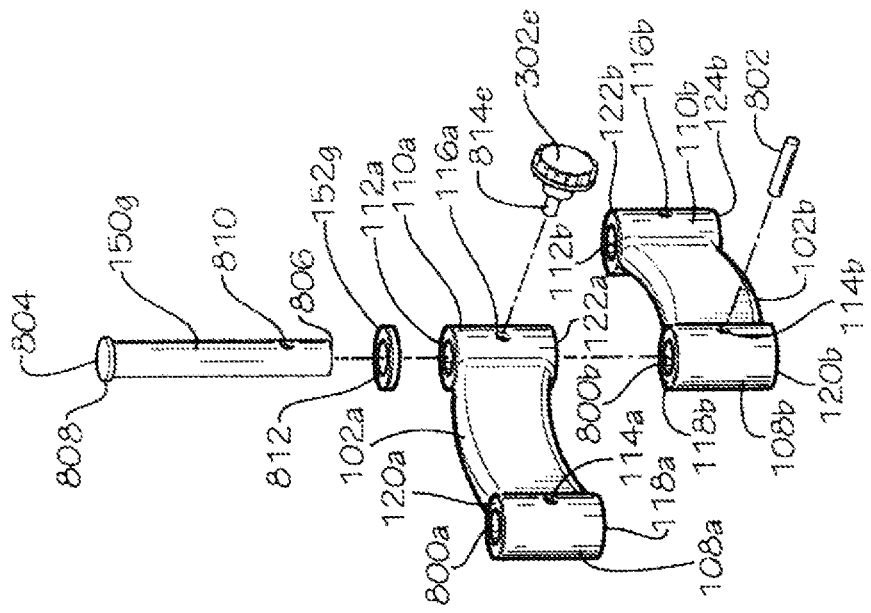
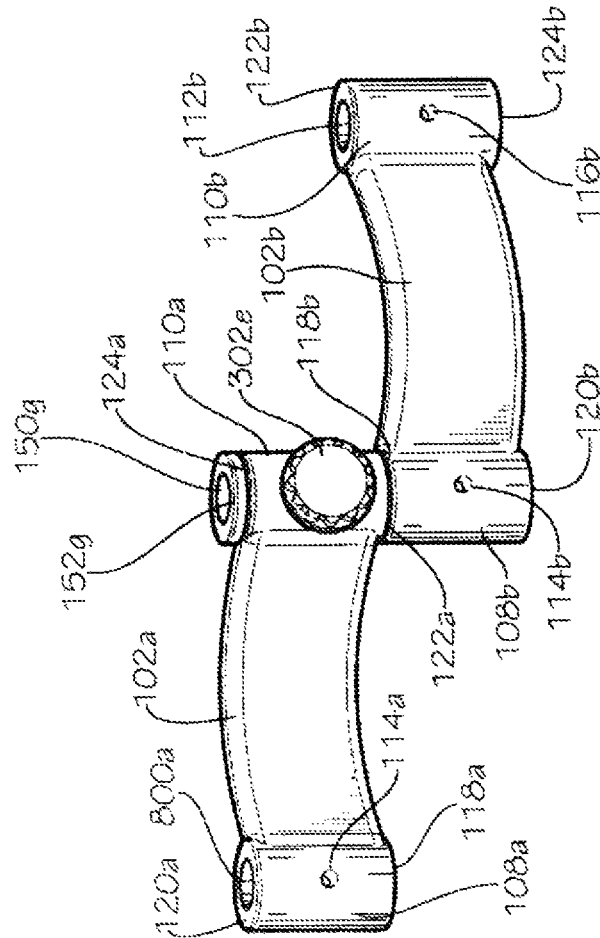

DOUBLE ARM POST SUPPORT ASSEMBLY

REFERENCE TO RELATED APPLICATIONS

This application claims the benefit of U.S. Provisional Application No. 61/993,555, filed May 15, 2014, which is hereby specifically incorporated by reference herein in its entirety.

TECHNICAL FIELD

The present disclosure relates generally to medical equipment support systems. More specifically, the present disclosure relates to a modular medical equipment support system for reliably, safely, and securely supporting life support apparatus in limited space environments.

BACKGROUND

In the daily care of patients, a great diversity of medical equipment, including infusion management equipment and supplies, pressure transducers, physiological monitors and other equipment is employed. Such equipment typically is set up at the patient's bedside where it is supported by various stands, racks or hangers. For example, the equipment may be supported by 5-star floor stands, attached to headwalls, suspended from booms that are affixed to the ceiling, floor or wall mounted columns, or on other stationary or mobile platforms.

A difficulty arises in certain specialized hospitals units where the available space for the support of all of the needed equipment is limited. In those cases, the available space for all of the needed equipment is often limited to a single wall mounted column, rail, or other support structure. The equipment gets cumbersome and cluttered and becomes difficult to manage and organize. Further, the lines, tubing, cords and monitor cables all become disorganized and tangled. As a result such an environment becomes difficult to manage.

SUMMARY

Disclosed is a support arm assembly comprising: a support arm, the support arm including a support arm connector hub and a support arm body; and a split arm, the split arm including a split arm connector hub and a support hub, the split arm connector hub connecting to the support arm connector hub.

Also disclosed is a method comprising: mounting a split arm assembly on a structure, the split arm assembly including a support arm, the support arm including a support arm hub and a support arm body, and a split arm, the split arm including a split arm connector hub and a support hub, the split arm connector hub connecting to the support arm connector hub; supporting an item at the support hub; and moving the split arm relative to the support arm.

Various implementations described in the present disclosure may include additional systems, methods, features, and advantages, which may not necessarily be expressly disclosed herein but will be apparent to one of ordinary skill in the art upon examination of the following detailed description and accompanying drawings. It is intended that all such systems, methods, features, and advantages be included within the present disclosure and protected by the accompanying claims.

BRIEF DESCRIPTION OF THE DRAWINGS

The features and components of the following figures are illustrated to emphasize the general principles of the present disclosure. Corresponding features and components throughout the figures may be designated by matching reference characters for the sake of consistency and clarity.

FIG. 7 is a perspective view of a joint connecting two support arms.

FIG. 8 is an exploded view of the joint of FIG. 8.

DETAILED DESCRIPTION

Figure 1:
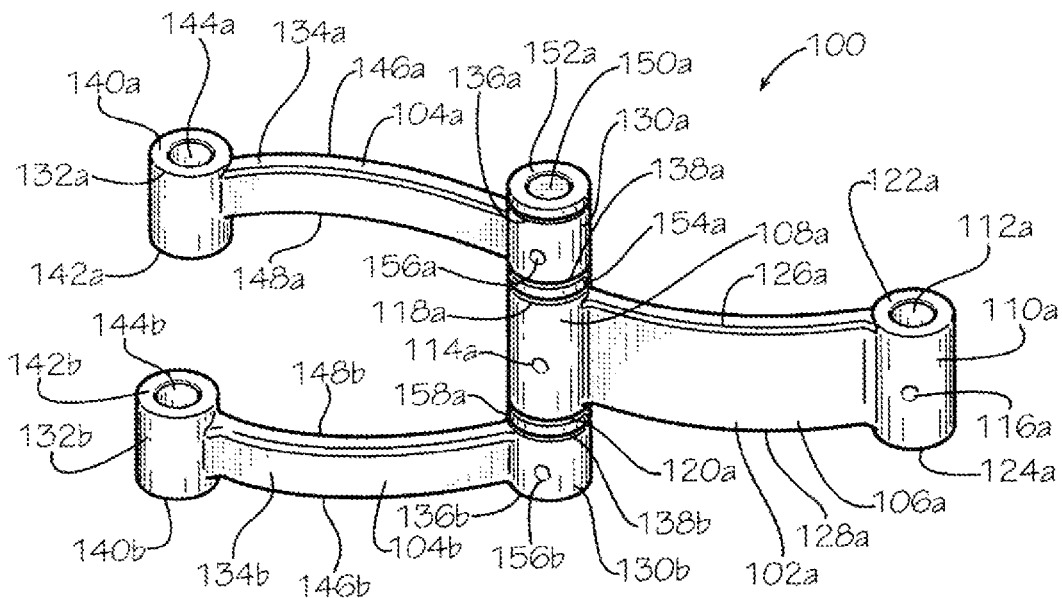
FIG. 1 is a perspective view of a support arm assembly including a support arm and a pair of split arms in accordance with an embodiment of the current disclosure.

In view of the shortcomings of known medical equipment transfer systems, the present disclosure provides a support system for efficiently supporting and organizing all of the various equipment employed in the daily care of patients. There is therefore a need for a modular system for supporting patient life support and care equipment, in addition to various other types of equipment, that is of low mechanical complexity, and that utilizes fewer, standardized, simpler components to permit low-cost manufacturing and reduced service and warranty costs by minimizing field maintenance. There is still a further need for a patient equipment support system that minimizes crevices, exposed fasteners, and upward-facing cavities to facilitate effective cleaning and infection control. There is yet a further need for a patient equipment support system that permits nursing staff to position and re-position the support equipment relative to the patient that allows ready access to the patient and facilitates easy monitoring and control of life-support equipment, minimizes the total footprint of associated equipment, and minimizes the risk of dislodging fluid lines, cables and leads. Additionally, there is a need for a patient equipment system that is articulated to allow caregivers full freedom in repositioning the patient support equipment around the patient's head.

It is therefore an object of the present disclosure to provide a modular system for supporting patient life support and care equipment that is of low mechanical complexity, and that utilizes fewer, standardized, simpler components to permit low-cost manufacturing and reduced service and warranty costs by minimizing field maintenance. It is still a further object of the present disclosure to provide a patient equipment support system that minimizes crevices, exposed fasteners and upward-facing cavities to facilitate effective cleaning and infection control. It is yet a further object of the present disclosure to provide a patient equipment support system that permits nursing staff to position and re-position the support equipment relative to the patient that allows ready access to the patient and facilitates easy monitoring and control of life-support equipment, minimizes the total footprint of associated equipment, and minimizes the risk of dislodging fluid lines, cables and leads. It is also an object of the present disclosure to provide a patient equipment system that is articulate to allow caregivers full freedom in repositioning the patient support equipment around the patient's head.

In this regard, the present disclosure provides a modular support arm system to reliably support a variety of patient care equipment in an efficient manner. The system generally includes a mounting clamp or other attachment mechanism at one end and at least one articulating arm segment that terminates in a pole clamp support or other attachment mechanism at another end. Further, in various embodiments, the arm allows for the interchangeable installation of a plurality of modular articulating arm segments that are joined to one another with a pivoting joint or other connecting mechanism. Further, the terminal end may include two pole support clamps. Still further, the clamp support end may also be configured to support two articulating arm segments in a manner that allows two articulating arms to extend from the mounting clamp.

The terminal end may include two arms wherein one arm may be used to support an equipment pole or other types of equipment. Further, the second arm may be stowed rearward when not needed, may be used in conjunction with the first arm to support a single pole, or may be used separately to support a second equipment pole or additional other types of equipment. This allows modularity yet provides a compact and space saving system.

In various embodiments, the mounting clamp may allow a modular arm segment to be mounted both above and below the clamp body thereby allowing two arms to extend from the same mounting clamp.

All of the modular arm segments, clamps and terminal ends may be joined in a pivotal fashion and employ bushings to allow smooth articulation and versatile positioning of the arms.

Disclosed is a support arm assembly and associated methods, systems, devices, and various apparatus. The support arm assembly includes a support arm and a split arm. It would be understood by one of skill in the art that the disclosed support arm assembly is described in but a few exemplary embodiments among many. No particular terminology or description should be considered limiting on the disclosure or the scope of any claims issuing therefrom.

One embodiment of a support arm assembly 100 is disclosed and described in FIG. 1. The support arm assembly 100 includes a plurality of articulating arm segments. In various embodiments, the articulating arm segments include a support arm 102a and a split arm 104a connected to the support arm 102a. In the present embodiment, the support arm assembly 100 includes a pair of split arms 104a,b; however, the number of split arms 104 should not be considered limiting on the current disclosure as in various other embodiments, the support arm assembly 100 may include any desired number of split arms 104, including no split arms 104. In addition, the number of support arms 102 should not be considered limiting on the current disclosure as in various other embodiments, the support arm assembly 100 may include any desired number of support arms 102 including no support arms 102.

The split arms 104 and the support arms 102 are reversible and any references to a "top" or "bottom" in the current disclosure are relative to the orientation shown in FIG. 1. The split arms 104 and support arms 102 may have either an orientation that is the same as shown in FIG. 1 or an orientation upside-down relative to the orientation shown in FIG. 1.

As shown in FIG. 1, the support arm 102a includes a support body 106a, a first connector hub 108a, and a second connector hub 110a. The first connector hub 108a has a top end 118a and a bottom end 120a. In various embodiments, the first connector hub 108a defines a first hub opening 800a (shown in FIG. 8) extending through the first connector hub 108a from the top end 118a to the bottom end 120a. The second connector hub 110a has a top end 122a and a bottom end 124a. In various embodiments, the second connector hub 110a defines a second hub opening 112a extending through the second connector hub 110a from the top end 122a to the bottom end 124a. In various embodiments, the first hub opening 800a and second hub opening 112a are dimensioned to accept joint rods, such as a rod 150a and a rod 150g (shown in FIG. 3), inserted through the respective hub openings 800a,112a, as described in greater detail below.

As shown in FIG. 1, in various embodiments, the first connector hub 108a defines a first pin opening 114a extending transversely through the first connector hub 108a and the second connector hub 110a defines a second pin opening 116a extending transversely through the second connector hub 110a. The connector hubs 108a,110a may have a generally tubular shape; however, the shape of the connector hubs 108a,110a should not be considered limiting on the current disclosure as in various other embodiments, the connector hubs 108a,110a may be angled, rectangular, oblong, oval, or have any other desired shape. In various embodiments, the first pin opening 114a or the second pin opening 116a may extend transversely through a part of the respective connector hubs 108a,110a or entirely through the connector hubs 108a,110a.

The support body 106a includes a top end 126a and a bottom end 128a. In various embodiments, a profile of the top end 126a is concave between the first connector hub 108a and the second connector hub 110a and a profile of the bottom end 128a is convex between the first connector hub 108a and the second connector hub 110a. The shape of the support body 106a should not be considered limiting on the current disclosure as in various other embodiments, the support body 106a may be rectangular, angled, curved, oblong, or have any other desired shape. In various embodiments with a plurality of support arms 102, the shape of the support body 106a of one support arm 102a may be different from the shape of the support body 106 of another support arm 102.

Each split arm 104a,b includes a split arm body 134a,b, a third connector hub 130a,b and a support hub 132a,b, respectively. In the present embodiment, the split arm 104b is in an upside-down orientation compared to the split arm 104a. In various embodiments, the split arms 104a,b may be attached in either orientation.

As shown in FIG. 1, each third connector hub 130a,b has a top end 136a,b and a bottom end 138a,b. In various embodiments, each third connector hub 130a,b defines a third hub opening (not shown) extending through each respective third connector hub 130a,b from the top end 136a,b to the bottom end 138a,b. The connector hubs 130a,b may have a generally tubular shape; however, the shape of the connector hubs 130a,b should not be considered limiting on the current disclosure as in various other embodiments, the connector hubs 130a,b may be angled, rectangular, oblong, oval, or have any other desired shape. In various embodiments, the third hub openings are dimensioned to accept a joint rod, such as the rod 150a, inserted through the third hub openings as described in greater detail below. As shown in FIG. 1, in various embodiments, each third connector hub 130a,b defines a third pin opening 156a,b extending transversely through each third connector hub 130a,b. In various embodiments, the third pin openings 156a,b may extend transversely through a part of the respective third connector hubs 130a,b or entirely through the third connector hubs 130a,b.

Each support hub 132a,b of the respective split arms 104a,b has a top end 140a,b and a bottom end 142a,b, respectively. In various embodiments, each respective support hub 132a,b defines a support opening 144a,b extending through the support hub 132a,b from the top end 140a,b to the bottom end 142a,b. In various embodiments, the support openings 144a,b are dimensioned to accept a support post, such as an IV pole 304a (shown in FIG. 3), inserted through the support openings 144a,b as described in greater detail below. In the present embodiment, the third connector hubs 130a,b and support hubs 132a,b have a generally tubular shape; however, the shape of the third connector hubs 130a,b and support hubs 132a,b should not be considered limiting on the current disclosure as in various other embodiments, the connector hubs 130a,b and support hubs 132a,b may be angled, rectangular, oblong, or have any other desired shape.

In various embodiments, each split arm body 134a,b has a top end 146a,b and a bottom end 148a,b, respectively. A profile of the top end 146a,b may be concave between the third connector hub 130a,b and the support hub 132a,b and a profile of the bottom end 148a,b a may be convex between the third connector hub 130a,b and the support hub 132a,b. However, the shape of the each split arm body 134a,b should not be considered limiting on the current disclosure as in various other embodiments, each split arm body 134a,b may be rectangular, angled, or have any other desired shape. In various other embodiments, the split arm body 134a may have a shape that is different from the split arm body 134b. The orientation of the split arms 104a,b or the support arm 102a should not be considered limiting on the current disclosure.

The split arms 104a,b are connected to the support arm 102a through a joint such that each split arm 104a,b is movable relative to the support arm 102a. In the present embodiment, the joint is a pin joint including the rod 150a and a collar 152a. Each split arm 104a,b and support arm 102a may be rotatable and thereby movable on the rod 150a relative to the other arms.

Figure 10:
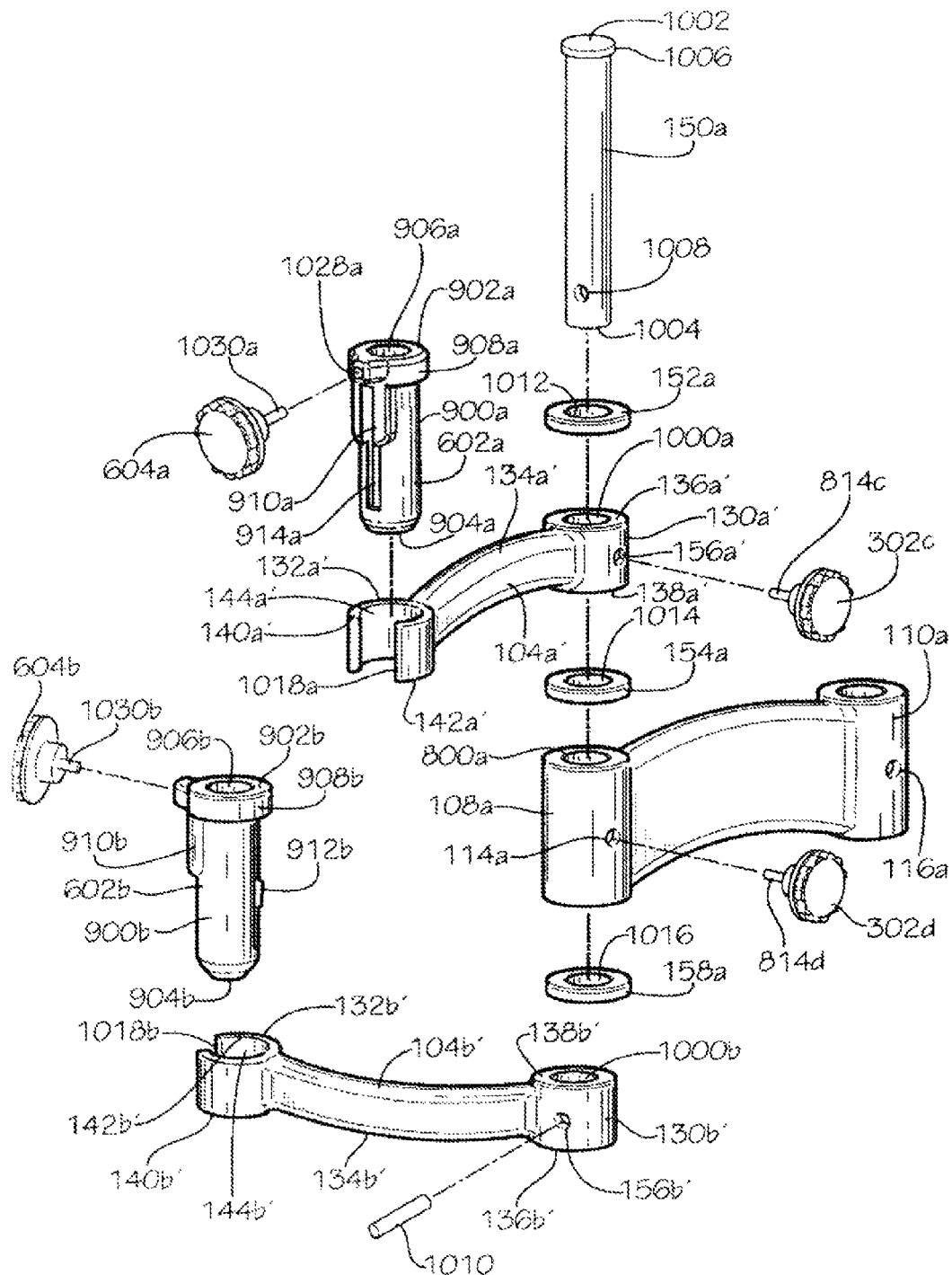
FIG. 10 is an exploded view of the joint of FIG. 9.

In various embodiments with the pin joint, the rod 150a may include a rod opening 1008 (shown in FIG. 10) dimensioned to accept a securing pin 1010 (shown in FIG. 10). In various embodiments, the securing pin 1010 is inserted into the lowermost pin opening at a joint, either on one of the split arms 104a,b or the support arm 102a, and into the rod opening 1008 to lock the rod 150a in place. The rod 150a is inserted through the collar 152a, the third connector hub 130a, a first spacer 154a, the first connector hub 108a, a second spacer 158a, and the third connector hub 130b. The first spacer 154a and second spacer 158a may not be present in various embodiments. The securing pin 1010 may be inserted into the third pin opening 156b of the split arm 104b in the present embodiment. In this manner, the collar 152a and the securing pin 101 retain the rod 150a through the third connector hubs 130a,b, the first connector hub 108a, and the spacers 154a,158a. The secured rod 150a connects the split arms 104a,b and the support arm 102a in various embodiments.

In various embodiments, the split arm 104a and support arm 102a are rotatable about the rod 150a such that split arm 104a and support arm 102a are movable relative to the split arm 104b secured to the rod 150a through the securing pin 1010. In various embodiments, as described in greater detail below, the support arm assembly 100 may include securing knobs having pins or screws, which may be similar to a securing knob 302e having a knob pin 814e as shown in FIG. 8, insertable into the first pin opening 114a in the first connector hub 108a of the support arm 102a or the third pin opening 156a of the split arm 104a. In these embodiment, the securing knobs and pins may engage the rod 150a to secure the split arm 104a or support arm 102a relative to the rod 150a. In various other embodiments, other securing mechanisms may be utilized to secure the split arm 104a or support arm 102a relative to the rod 150a.

Figure 2:
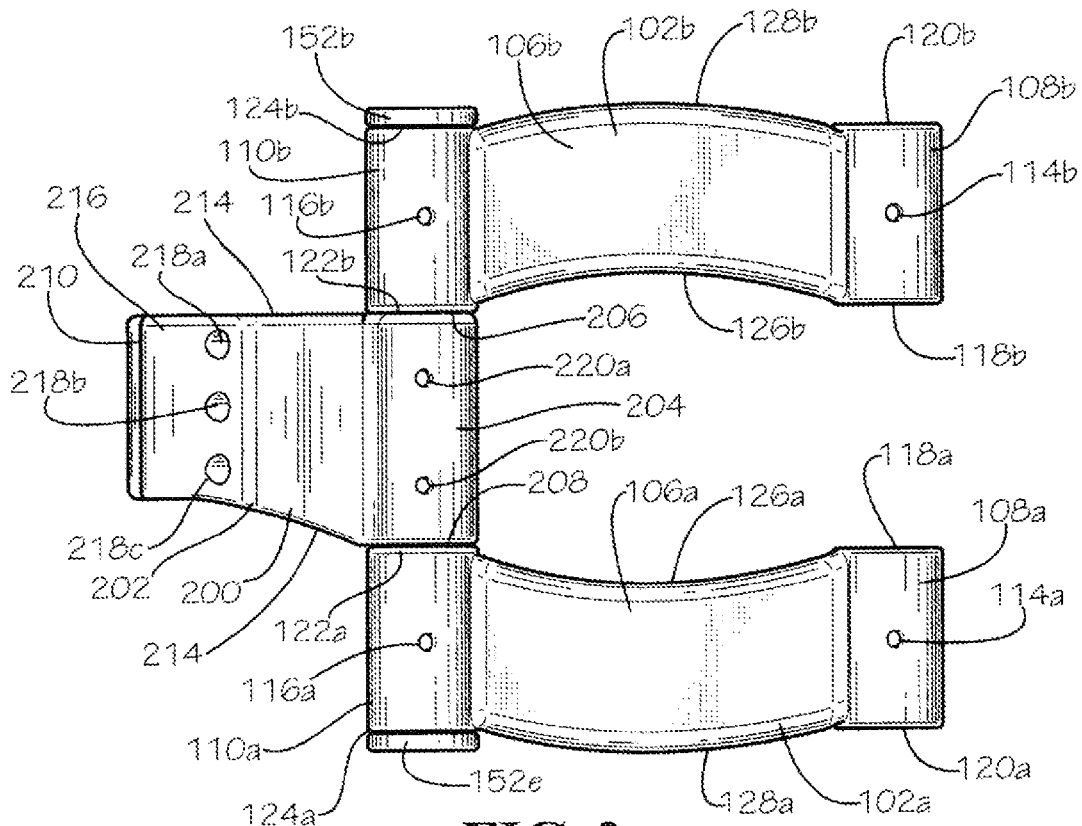
FIG. 2 is a side view of the support arm of FIG. 1 connected to another support arm and a mounting arm.

FIG. 2 shows the support arm 102a and another support arm 102b connected to a mounting arm 200. Although two support arms 102a,b are shown connected to the mounting arm 200, the number of support arms connected to the mounting arm 200 should not be considered limiting on the current disclosure as in various other embodiments, the support arm assembly 100 includes any desired number of support arms 102 connected to the mounting arm 200, including no support arms 102.

The support arm 102b is similar to support arm 102a but is in an upside-down orientation compared to support arm 102a. In various embodiments, the support arms 102a,b may be attached in either orientation. The support arm 102b includes a support body 106b, a first connector hub 108b, and a second connector hub 110b. The first connector hub 108b has a top end 118b and a bottom end 120b. The first connector hub 108b defines a first hub opening 800b (shown in FIG. 8) extending through the first connector hub 108b from the top end 118b to the bottom end 120b. The second connector hub 110b has a top end 122b and a bottom end 124b. The second connector hub 110b defines a second hub opening 112b (shown in FIG. 7) extending through the second connector hub 110b from the top end 122b to the bottom end 124b. In various embodiments, the first hub opening 800b and the second hub opening 112b are dimensioned to accept a joint rod, such as a joint rod similar to rod 150a, inserted through the respective hub openings 112b, 800b as described in greater detail below. The first connector hub 108b may define a first pin opening 114b extending transversely through the first connector hub 108b and the second connector hub 110b may define a second pin opening 116b extending transversely through the second connector hub 110b. The support body 106b includes a top end 126b and a bottom end 128b.

As shown in FIG. 2, the mounting arm 200 includes a mounting body 202, a mounting hub 204, and a connecting end 210. The mounting hub 204 includes a top end 206 and a bottom end 208. In various embodiments, the mounting hub 204 defines a mounting opening (not shown) extending through the mounting hub 204 from the top end 206 to the bottom end 208. The mounting opening may be dimensioned to accept a joint rod, such as a joint rod 150b shown in FIG. 5, inserted through the mounting opening, as described in greater detail below. In various embodiments, the mounting hub 204 defines a first mounting pin opening 220a and a second mounting pin opening 220b extending transversely through the mounting hub 204; however, the number or location of the pin openings 220a,b should not be considered limiting on the current disclosure. In various embodiments, the first mounting pin opening 220a and the second mounting pin opening 220b may extend transversely through a part of the mounting hub 204 or entirely through the mounting hub 204.

In the present embodiment, the support arms 102a,b are assembled such that the support arm 102a is positioned below the mounting hub 204 and the support arm 102b is positioned above the mounting hub 204. In the present embodiment, there are no spacers positioned between the second connector hubs 110a,b and the mounting hub 204 and the second connector hub 110b contacts the top end 206 of the mounting hub 204 and the second connector hub 110a contacts the bottom end 208 of the mounting hub 204; however, in various embodiments, spacers such as spacer 154a or spacer 158a, may be positioned on the joint rod between the second connector hub 110a and the mounting hub 204 and between the second connector hub 110b and the mounting hub 204. The positioning of the support arms 102a,b relative to the mounting hub 204 should not be considered limiting on the current disclosure as in various other embodiments, either support arm 102a,b may be above or below the mounting hub 204, both support arms 102a,b may be above the mounting hub 204, or both support arms 102a,b may be below the mounting hub 204.

In various embodiments, the mounting body 202 includes a top end 212 and a bottom end 214. In various embodiments, a profile of the top end 212 is linear and a profile of the bottom end 214 is arcuate; however, the profile of the top end 212 or the bottom end 214 should not be considered limiting as in various other embodiments, the top end 212 or bottom end 214 may have any desired shape.

The connecting end 210 of the mounting arm 200 enables the mounting arm 200 to connect with a mounting mechanism which may engage a single wall mounted column, rail, or other support structure found in a medical setting. In the present embodiment, the mounting mechanism is a clamp including a first half-round segment 216 and a second half-round segment 310 (shown in FIG. 3). In various embodiments, the first half-round segment 216 is integrally formed with the mounting arm 200; however, in various other embodiments, the first half-round segment 216 is connected to the mounting arm 200 through various connecting mechanisms such as screws, bolts, pins, and various similar mechanisms. Together, the half-round segments 216, 310 define a clamp opening 302 (shown in FIG. 3). The size of the clamp opening 302 may be adjusted to accommodate various support structures in the medical setting. In the present embodiments, the clamp opening 302 is adjusted by tightening clamp screws 218a,b,c connecting the first half-round segment 216 to the second half-round segment 310. The number of clamp screws 218a,b,c should not be considered limiting on the current disclosure as in various embodiments, the clamp may include any number of clamp screws, including no clamp screws. In various other embodiments, the clamp may be adjusted through mechanisms other than clamp screws 218a,b,c. The disclosure of the clamp as the mounting mechanism should not be considered limiting as in various other embodiments, the mounting mechanism may be hooks, pins, clasps, brackets, braces, rails, screws, nuts and bolts, or various other mechanisms suitable for mounting the support arm assembly 100 to a structure.

The support arms 102a,b are connected to the mounting arm 200 through a joint such that each support arm 102a,b is movable relative to the mounting arm 200. In the present embodiment, the joint is a pin joint including the rod 150b (shown in FIG. 5), which is similar to the rod 150a, a collar 152b, which is similar to the collar 152a, an additional rod (not shown), which is similar to the rods 150a,b, and a collar 152e, which is similar to the collar 152a.

The rod 150b is inserted through the collar 152b, the second hub opening 112b of the second connector hub 110b, and an upper half of the mounting opening (not shown). A first securing pin (not shown) may be inserted into the mounting pin opening 220a. In this manner, the first securing pin and collar 152b retain the first rod through the second connector hub 110b and a portion of the mounting hub 204. The support arm 102b is rotatable about the first rod such that the support arm 102b is movable relative to the mounting arm 200, which is secured to the first rod through the first securing pin.

The additional rod is inserted through the collar 152e, the second hub opening 112a of the second connector hub 110a, and a lower half of the mounting opening (not shown). A second securing pin (not shown) may be inserted into the mounting pin opening 220b. In this manner, the second securing pin and collar 152e retain the second rod through the second connector hub 110a and a portion of the mounting hub 204. The support arm 102a is rotatable about the second rod such that the support arm 102a is movable relative to the mounting arm 200, which is secured to the second rod through the second securing pin.

In various other embodiments, the joint may include a single rod, rather than rod 150b and the additional rod, inserted through the collar 152b, the second connector hub 110b, the mounting hub 204, and the second connector hub 110a. In these embodiments, the collar 152e may be omitted. A securing pin (not shown) may be inserted into the second pin opening 116a of the support arm 102a. In this manner, the collar 152b and the securing pin retain the rod through the second connector hubs 110a,b and the mounting hub 204, thereby connecting the support arms 102a,b and mounting arm 200. In various embodiments, the support arm 102b and mounting arm 200 are rotatable about the rod such that support arm 102b and mounting arm 200 are movable relative to the support arm 102a secured to the rod through the securing pin. In various embodiments, as described in greater detail below, the support arm assembly 100 may include securing knobs and pins insertable into the second pin opening 116b in the first connector hub 108b of the support arm 102b and/or the pin openings 220a,b of the mounting arm 200. In these embodiments, the securing knobs and pins may engage the rod to secure the mounting arm 200 or support arm 102b relative to the rod. In various other embodiments, other securing may be utilized to secure the mounting arm 200 or support arm 102b relative to the rod.

Figure 3:
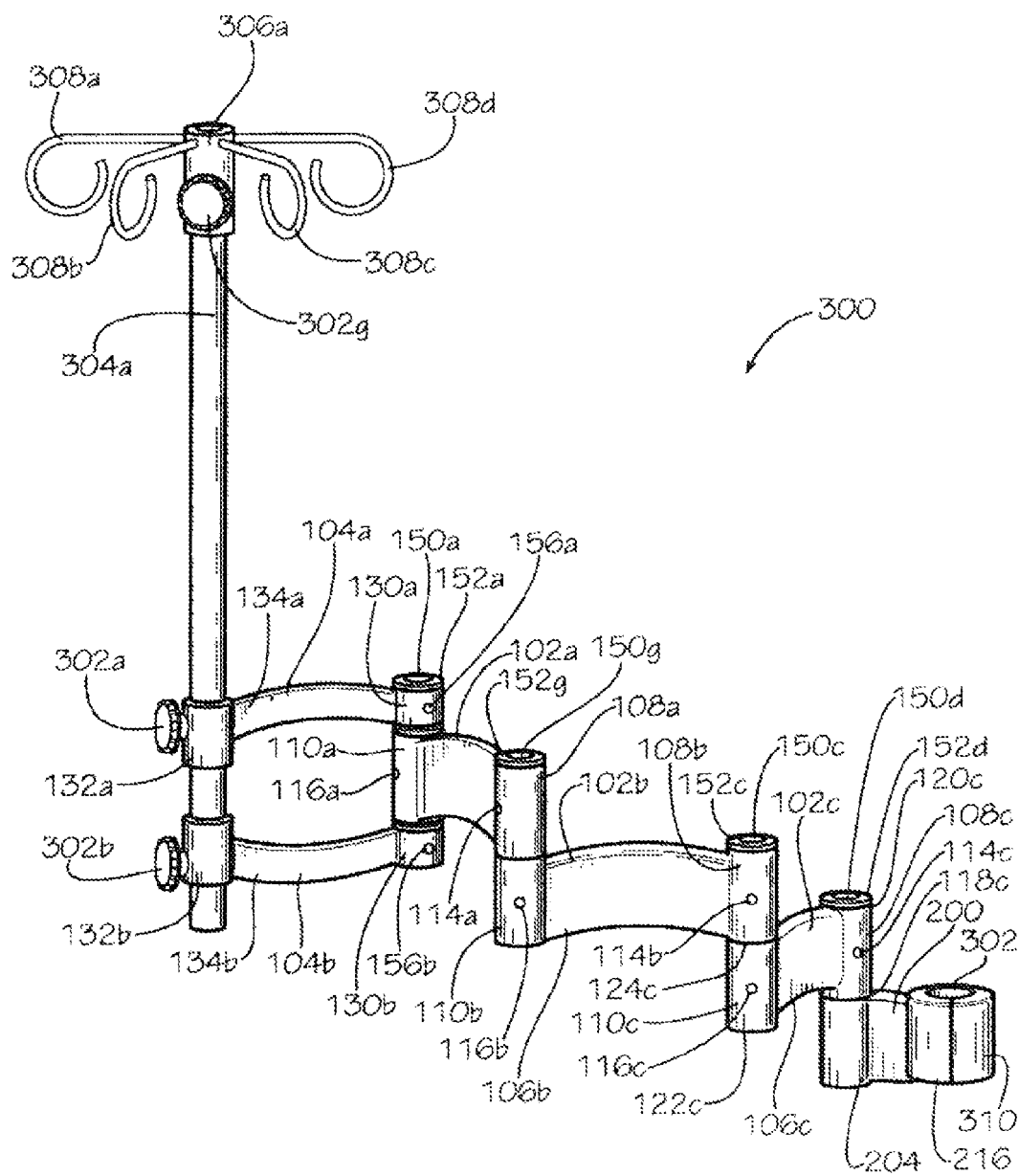
FIG. 3 is a perspective view of the support arm assembly of FIG. 1 with the pair of split arms supporting an IV post and including a plurality of support arms and a mounting arm.

FIG. 3 shows a support arm assembly 300 including support arms 102a,b,c and split arms 104a,b. In the present embodiment, the support arms 102a,b,c are in an upside-down orientation compared to the orientation of the support arm 102a shown in FIG. 1. The support arm 102c is similar to support arms 102a,b and includes a support body 106c, a first connector hub 108c, and a second connector hub 110c. As previously described, support arm 102c is in an upside-down orientation compared to the orientation of the support arm 102s shown in FIG. 1. The first connector hub 108c has a top end 118c, a bottom end 120c, and defines a first hub opening (not shown) extending through the first connector hub 108c from the top end 118c to the bottom end 120c. The second connector hub 110c has a top end 122c, a bottom end 124c, and defines a second hub opening (not shown) extending through the second connector hub 110c from the top end 122c to the bottom end 124c. In various embodiments, the first hub opening and second hub opening are dimensioned to accept a joint rod (not shown) inserted through the hub openings as described in greater detail below. The first connector hub 108b may define a first pin opening 114b extending transversely through the first connector hub 108b and the second connector hub 110b may define a second pin opening 116b extending transversely through the second connector hub 110b. The support body 106b includes a top end 126b and a bottom end 128b. As shown in FIG. 3, in various embodiments, the first connector hub 108c defines a first pin opening 114c extending transversely through the first connector hub 108c and the second connector hub 110c defines a second pin opening 116c extending transversely through the second connector hub 110c. The connector hubs 108c,110c may have a generally tubular shape; however, the shape of the connector hubs 108c,110c should not be considered limiting on the current disclosure as in various other embodiments, the connector hubs 108c,110c may be angled, rectangular, oblong, oval, or have any other desired shape. In various embodiments, the first pin opening 114c or the second pin opening 116c may extend transversely through a part of the respective connector hubs 108c,110c or entirely through the connector hubs 108c,110c.

As shown in FIG. 3, the support arm 102a is connected to the support arm 102b through a pin joint including a rod 150g and collar 152g. A securing pin, which may be similar to a securing pin 802 shown in FIG. 8, may be inserted into the second pin opening 116b to retain the rod 150g in the first connector hub 108a and the second connector hub 110b. The first connector hub 108a is positioned above the second connector hub 110b in the present embodiment; however, the positioning of should not be considered limiting on the current disclosure.

The support arm 102b is connected to the support arm 102c through a pin joint including a rod 150c and a collar 152c. A securing pin (not shown) may be inserted into a second pin opening 116c of the second connector hub 110c to retain the rod 150c in the first connector hub 108b and second connector hub 110c. The first connector hub 108b is positioned above the second connector hub 110c in the present embodiment; however, the positioning should not be considered limiting on the current disclosure.

The support arm 102c is connected to the mounting arm 200 through a pin joint including a rod 150d and a collar 152d. A securing pin (not shown) may be inserted into one of the mounting pin openings 220a,b of the mounting hub 204 to retain the rod 150d in the first connector hub 108c and mounting hub 204. The first connector hub 108c is positioned above the mounting hub 204 in the present embodiment; however, the positioning should not be considered limiting on the current disclosure.

As previously described, the support arm 102a is connected to the split arms 104a,b through the pin joint including the rod 150a and collar 152a. The orientation or positioning of any of the support arms 102a,b,c or split arms 104a,b relative to each other should not be considered limiting on the current disclosure as in various embodiments, the support arms 102a,b,c and split arms 104a,b may have any desired orientation or positioning.

As shown in FIG. 3, each support hub 132a,b includes a securing knob 302a,b. Each securing knob 302a,b includes an engagement pin or screw that is insertable into support pin openings (not shown) on each respective support hub 132a,b. FIG. 3 shows an IV pole 304a inserted through both support openings 144a,b, though other pieces of medical equipment other than an IV pole 304a may be inserted in various other embodiments; however, in various embodiments, the IV pole 304a may be inserted through one or both support openings 144a,b of the support hubs 132a,b. As shown in FIG. 3, in various embodiments, the IV pole 304a may include a cap 306a having a plurality of hooks 308a, b,c,d to support various cabling, tubing, bags, or other medical equipment. The number, shape, or location of the hooks 308 should not be considered limiting on the current disclosure. In various other embodiments, the hooks 308a, b,c,d may be integrally formed with the IV pole 304a. In various embodiments, the cap 306a includes a securing knob 302g. The shape or design of the IV pole 304a should not be considered limiting on the current disclosure.

The securing knobs 302a,b,g may be tightened such that the engagement pin or screw engages the IV pole 304a in the support openings 144a,b or through the cap 306a to lock the IV pole 304a at a desired vertical position relative to the support arm assembly 100'''' or cap 306a. The disclosure of the IV pole 304a should not be considered limiting on the current disclosure as in various other embodiments, the medical equipment may be any medical equipment to be supported by the support arm assembly 300, such as diagnostic equipment, insulin pumps, or heart or other vital sign monitors.

Figure 4:
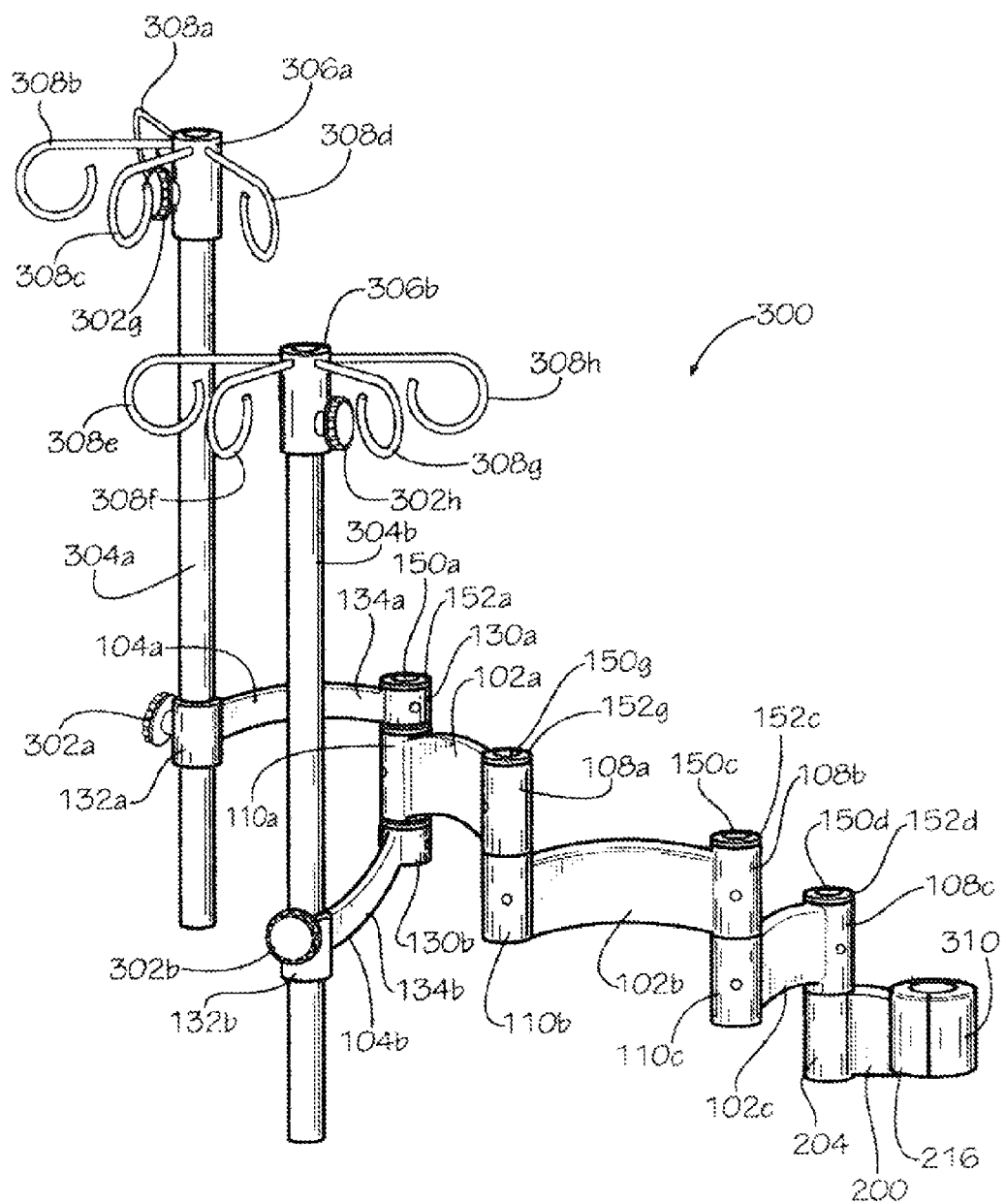
FIG. 4 is a perspective view of the support arm assembly of FIG. 1 with the pair of split arms each supporting an IV post and including a plurality of support arms and a mounting arm.

FIG. 4 shows the support arm assembly 300 with the split arm 104a supporting the IV pole 304a through the support opening 144a in the support hub 132a and the split arm 104b supporting another IV pole 304b through the support opening 144b in the support hub 132b. Similar to IV pole 304a, IV pole 304b may include a cap 306b including a plurality of hooks 308e,f,g,h. The cap 306b may also include a securing knob 302h, which is substantially similar to securing knob 302g. As shown in FIG. 4 and compared to FIG. 3, the split arms 104a,b may be rotated relative to the support arm 102a through the pin joint and thereby position the IV poles 304a,b at a desired location relative to the support arm 102a. FIG. 4 also shows the support arms 102a,b,c rotated relative to each other and the mounting arm 200 compared to the orientation shown in FIG. 3.

Figure 5:
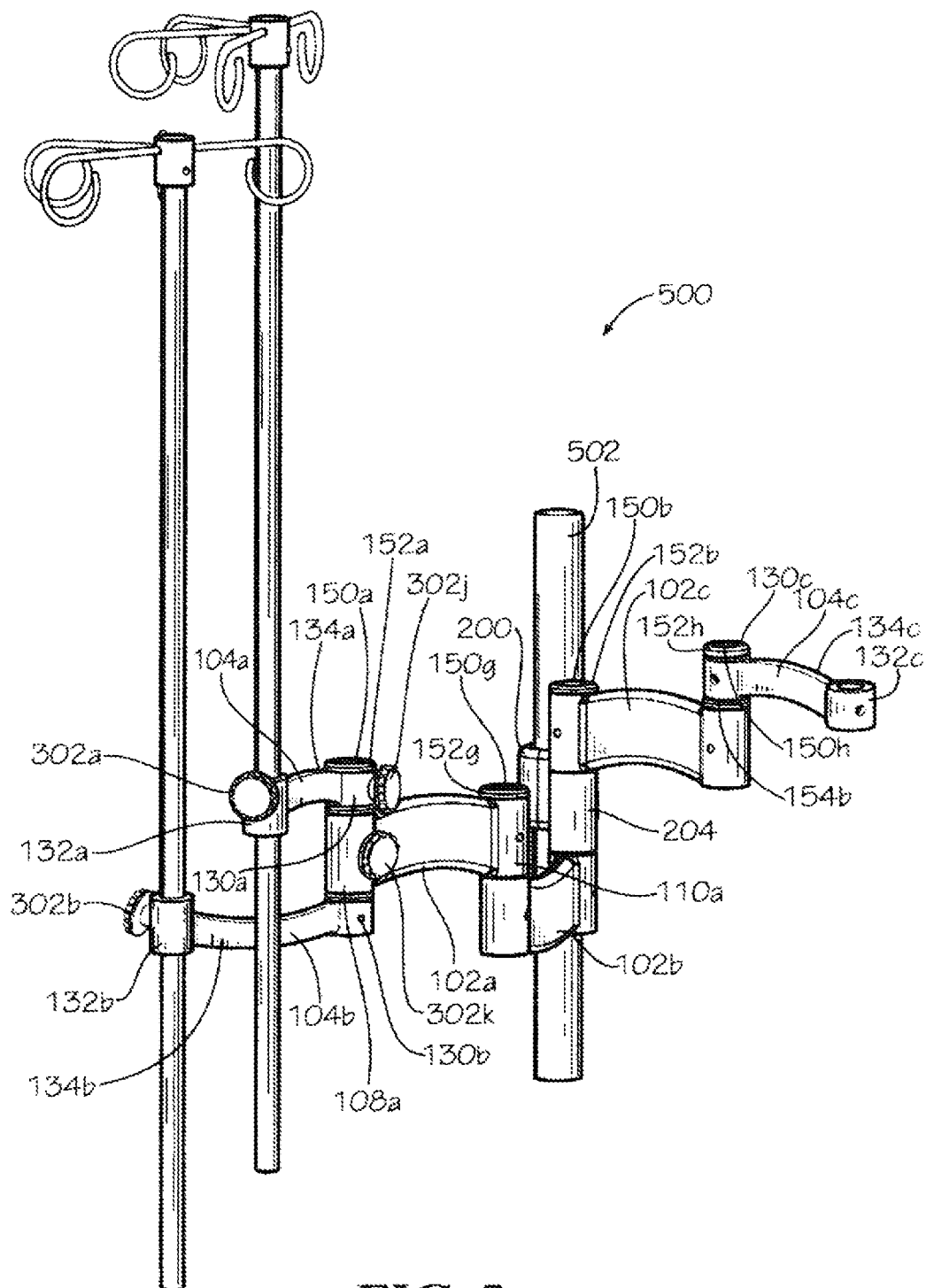
FIG. 5 is a perspective view of another embodiment of a support arm assembly mounted on a post and including a mounting arm, three support arms, and three split arms.

FIG. 5 shows another embodiment of a support arm assembly 500 mounted on a structure within the medical setting. In the present embodiment, the support arm assembly 500 is mounted on a post 500; however, in various other embodiments, the support arm assembly 500 may be mounted on any suitable structure for supporting the support arm assembly 500 such as a rail, bedpost, chair, or any other structure found in a medical setting.

As shown in FIG. 5, the support arm assembly 500 includes the support arm 102b and support arm 102c connected to the mounting arm 200 through the pin joint including the rod 150b and collar 152b. In various embodiments, the support arm 102c is positioned above the mounting hub 204 and the support arm 102b is positioned below the mounting hub 204. A split arm 104c is connected to the support arm 102c through a pin joint including a rod 150h and collar 152h, which may be similar to the rod 150a and collar 152a. In various embodiments, the support arm assembly 500 includes a spacer 154b on the rod 150h between the support arm 102c and the split arm 104c. The support arm 102a is connected to the support arm 102b through the pin joint including the rod 150g and collar 152g. The split arms 104a,b are connected to the support arm 102a through the pin joint including the rod 150a and collar 152a. The orientation and positioning of the support arms 102a,b,c and split arms 104a,b,c should not be considered limiting as in various other embodiments, any of the arms may be positioned or orientated as desired. In addition, the number of support arms 102a,b,c or split arms 104a,b,c should not be considered limiting on the current disclosure as in various other embodiments, the support arm assembly 500 may include any desired number of support arms 102a,b,c or any desired number of split arms 104a,b,c.

As shown in FIG. 5, in various embodiments, the support arm assembly 500 includes securing knobs 302j,k. In various embodiments, the securing knob 302j is inserted into the third pin opening 156a of the split arm 104a and the securing knob 302k is inserted into the first pin opening 114a of the support arm 102a. The respective securing knobs 302j,k may be tightened to secure the positions and thereby prevent rotation of the split arm 104a and support arm 102a respectively on the rod 150a as the securing knobs 302j,k engage the rod 150a.

Figure 6:
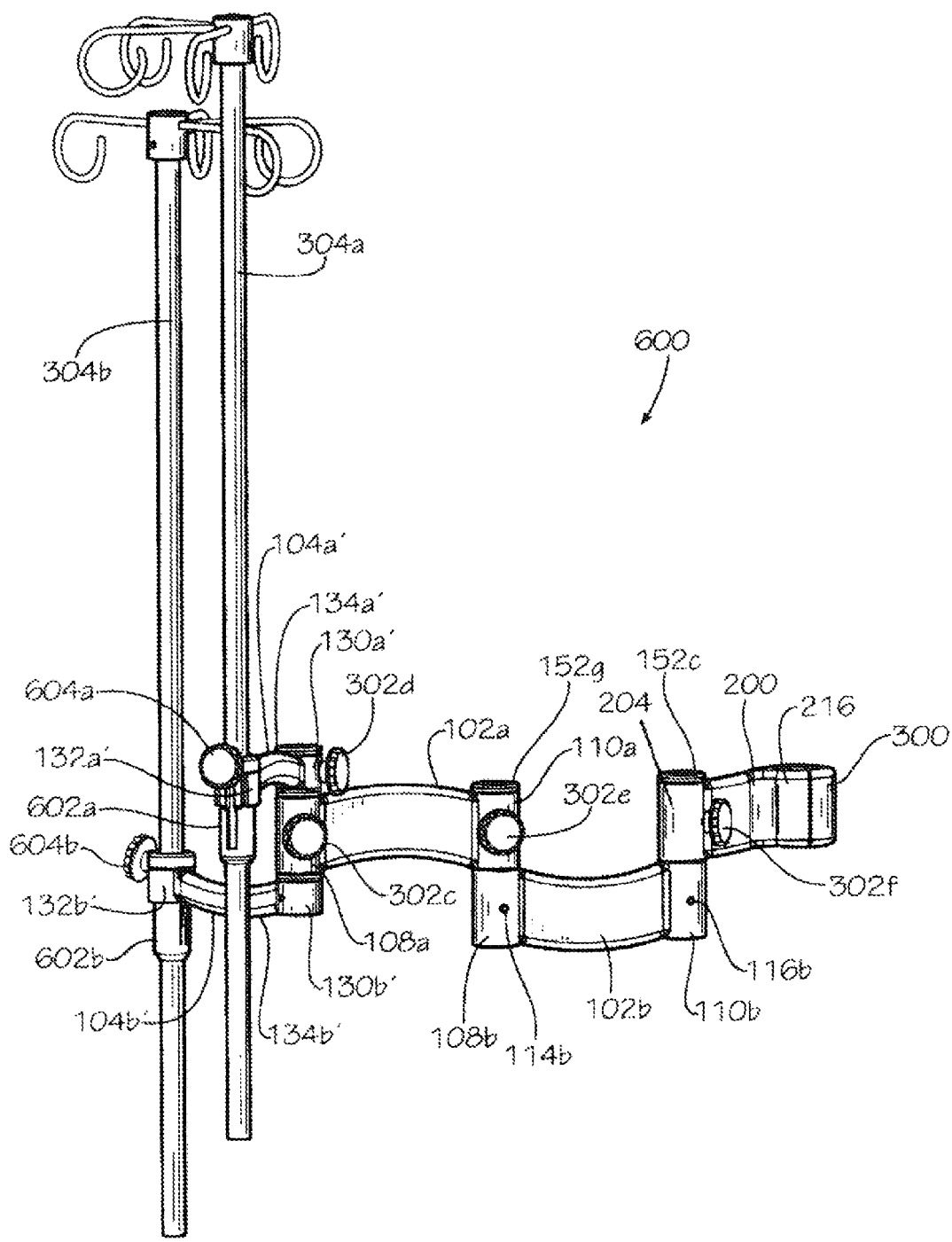
FIG. 6 is a perspective view of another embodiment of a support arm assembly including two support arms, a mounting arm, and another embodiment of a pair of split arms.

FIG. 6 shows another embodiment of a support arm assembly 600. As shown in FIG. 6, in various embodiments, the support arm assembly 600 includes the support arms 102a,b and split arms 104a',b'. The number of split arms 104' should not be considered limiting on the current disclosure as in various other embodiments, any desired number of split arms 104' may be utilized, including no split arms 104'. In various other embodiments, the support arm assembly 600 may include at least one split arm 104a and at least one split arm 104a'. The split arms 104' are reversible and reference to a "top" or "bottom" are relative to the orientation shown in FIG. 6. The split arms 104' may have either an orientation the same split arm 104a' as shown in FIG. 6 or an orientation upside-down relative to the orientation of split arm 104a' as shown in FIG. 6. In the present embodiment, the split arm 104b' is in an upside-down orientation compared to the split arm 104a'. In various embodiments, the split arms 104a',b' may be attached in either orientation. In the present embodiment, the support arm 102a is in an upside-down orientation compared to the orientation of support arm 102a in FIG. 1. Support arm 102b is in the same orientation as the orientation of support arm 102a in FIG. 1.

As shown in FIG. 6, the support arm assembly 600 includes the mounting arm 200. In the present embodiment, the support arm 102b is positioned below the mounting hub 204. The support arm 102b and mounting arm 200 are connected through the pin joint including the rod 150c (shown in FIGS. 3 and 4) and the collar 152c. The rod 150c is positioned through the mounting opening of the mounting hub 204 and the second hub opening 112b (shown in FIGS. 7 and 8). A securing pin (not shown) similar to the first securing pin 802 (shown in FIG. 8) is inserted into the second pin opening 116b to engage the rod 150c and secure the rod 150c in the mounting hub 204 and second connector hub 110b. Together, the collar 152c and securing pin may retain the rod 150c in the mounting hub 204 and connector hub 110b. In various embodiments, a securing knob 302f is inserted into one of the mounting pin openings 220a,b. The securing knob 302f may be tightened to secure the position and thereby prevent rotation of the mounting arm 200 relative to the support arm 102b about the rod 150c as a pin or screw of the securing knob 302f engages the rod 150c.

As shown in FIG. 6, in various embodiments, the second connector hub 110a is positioned above the first connector hub 108b. In various embodiments, the support hub 132a and the support hub 132b are connected through the pin joint including the rod 150g (shown in FIG. 8) and collar 152g. The rod 150g is positioned through the first hub opening 800b (shown in FIG. 8) of the first connector hub 108b and the second hub opening 112a (shown in FIGS. 7 and 8) of the second connector hub 110a. The first securing pin 802 (shown in FIG. 8) is inserted into the first pin opening 114b to engage the rod 150g and secure the rod 150g in the first connector hub 108b and second connector hub 110a. Together, the collar 152g and first securing pin 802 may retain the rod 150g in the first connector hub 108b and second connector hub 110a. In various embodiments, a securing knob 302e is inserted into the second pin opening 116a. The securing knob 302e may be tightened to secure the position of the support arm 102a relative to the support arm 102b about the rod 150g as the pin or screw of the securing knob 302e engages the rod 150g.

The split arms 104a',b' are positioned with the split arm 104a' above the first connector hub 108a and the split arm 104b' below the first connector hub 108a. In various embodiments, the split arms 104a',b' are connected through the pin joint including the rod 150a and collar 152a. The rod 150a is positioned through a third hub opening 1000a (shown in FIG. 10) of the split arm 104a', the first hub opening 800a (shown in FIG. 10) of the support hub 132a, and a third hub opening 1000b of the split arm 104b'. A securing knob 302c may be inserted into the first pin opening 114a and may be tightened to secure the position of the support arm 102a relative to the split arms 104a',b' about the rod 150a. A securing knob 302d may be inserted into a third pin opening 156a' of the split arm 104a' and may be tightened to secure the position of the split arm 104a' relative to the split arm 104b' and support arm 102a. The joint between the split arms 104a',b' is described in greater detail with reference to FIG. 10.

In the support arm assembly 600, similar to the support arm assembly 100, joints where the various support arms 102a,b, split arms 104a',b', and mounting arm are connected enable the various arms to be positioned relative to each other. In this manner, the support arm assembly 600 is an assembly with articulating arms so as to allow for flexibility in movement and positioning of any medical setting items, such as the IV poles 304a,b, supported by the support arm assembly 600.

As shown in FIG. 6, each split arm 104a',b' includes a third connector hub 130a',b', a split arm body 134a',b', and a support hub 132a',b'. The split arms 104a',b' are described in greater detail with reference to FIGS. 9, 10, and 15.

The support arm assembly 600 includes plugs 602a,b in various embodiments. The number of plugs 602 should not be considered limiting on the current disclosure as in various other embodiments, the support arm assembly 600 includes any number of plugs 602, including no plugs. As shown in FIG. 6, in various embodiments, each plug 602a,b includes a securing knob 604a,b. As described in greater detail below, each plug 602a,b may be installed on the IV poles 304a,b. The plugs 602a,b are described in greater detail below with reference to FIGS. 9-14.

FIGS. 7 and 8 show the joint where the support arm 102a and the support arm 102b are connected. The joint is a pin joint in various embodiments including the rod 150g and the collar 152g. As shown in FIG. 7, the first securing pin 802 is inserted through the first pin opening 114b to engaged the rod 150g and secure the rod 150g in the second connector hub 110a and the first connector hub 108b. Each first connector hub 108a,b defines the first hub opening 800a,b extending through the first connector hub 108a,b from the top end 118a,b to the bottom end 120a,b, respectively.

As shown in FIG. 8, the rod 150g includes a top end 804 and a bottom end 806. In various embodiments, the rod 150g defines a flange 808 at the top end 804. The flange 808 may be utilized to engage the collar 152g and retain the rod 150g in the second hub opening 112a and the first hub opening 800b when inserted into the first connector hub 108b and second connector hub 110a. As shown in FIG. 8, in various embodiments, the rod 150g defines a rod opening 810 extending transversely through the rod 150g. In various embodiments, the rod opening 810 may extend transversely through a part of the rod 150g or through the entire rod 150g. The rod opening 810 is dimensioned to accept the first securing pin 802. In various embodiments, the rod 150g defines a rod length from the top end 804 to the bottom end 806. The length of the rod 150g should not be considered limiting as the rod 150g may have any desired length to accommodate any number of support arms 102a,b, split arms 104a',b', and mounting arms 200 at the joint. In various embodiments, the rod opening 810 is defined on the rod 150g proximate to the bottom end 806 such that when the rod 150g is inserted into the hub openings to be joined, such as the first hub opening 800b and second hub opening 112a, the first securing pin 802 may be inserted into the pin opening, such as the first pin opening 114b, of the lowermost arm on the rod 150g, such as support arm 102b and into the rod opening 810.

As shown in FIG. 8, the collar 152g is annular in various embodiments and defines a collar opening 812. In various embodiments, the collar opening 812 is dimensioned to accept the rod 150g through the collar opening 812 but prevent the flange 808 from passing through the collar opening 812. When assembled, the collar opening 812, second hub opening 112a, and first hub opening 800b are aligned and accept the rod 150b through the respective openings.

The securing pin 802 is inserted through the first pin opening 114b and into the rod opening 810 such that the securing pin 802 is positioned in both the first pin opening 114b and the rod opening 810. In this manner, the rod 150g is secured in the joint through the securing pin 802 and the flange 808 interacting with the collar 152g.

As shown in FIG. 8, the securing knob 302e includes a knob pin 814e. In various embodiments, the knob pin 814e includes threading to engage the second pin opening 116a. The knob pin 814e is positioned in the second pin opening 116a and engages the second pin opening 116a. The knob pin 814e may be selectively tightened via the knob 302e to engage the rod 150g. Engagement of the knob pin 814e with the rod 150g may secure the support arm 102a in place on the rod 150g.

Figure 9:
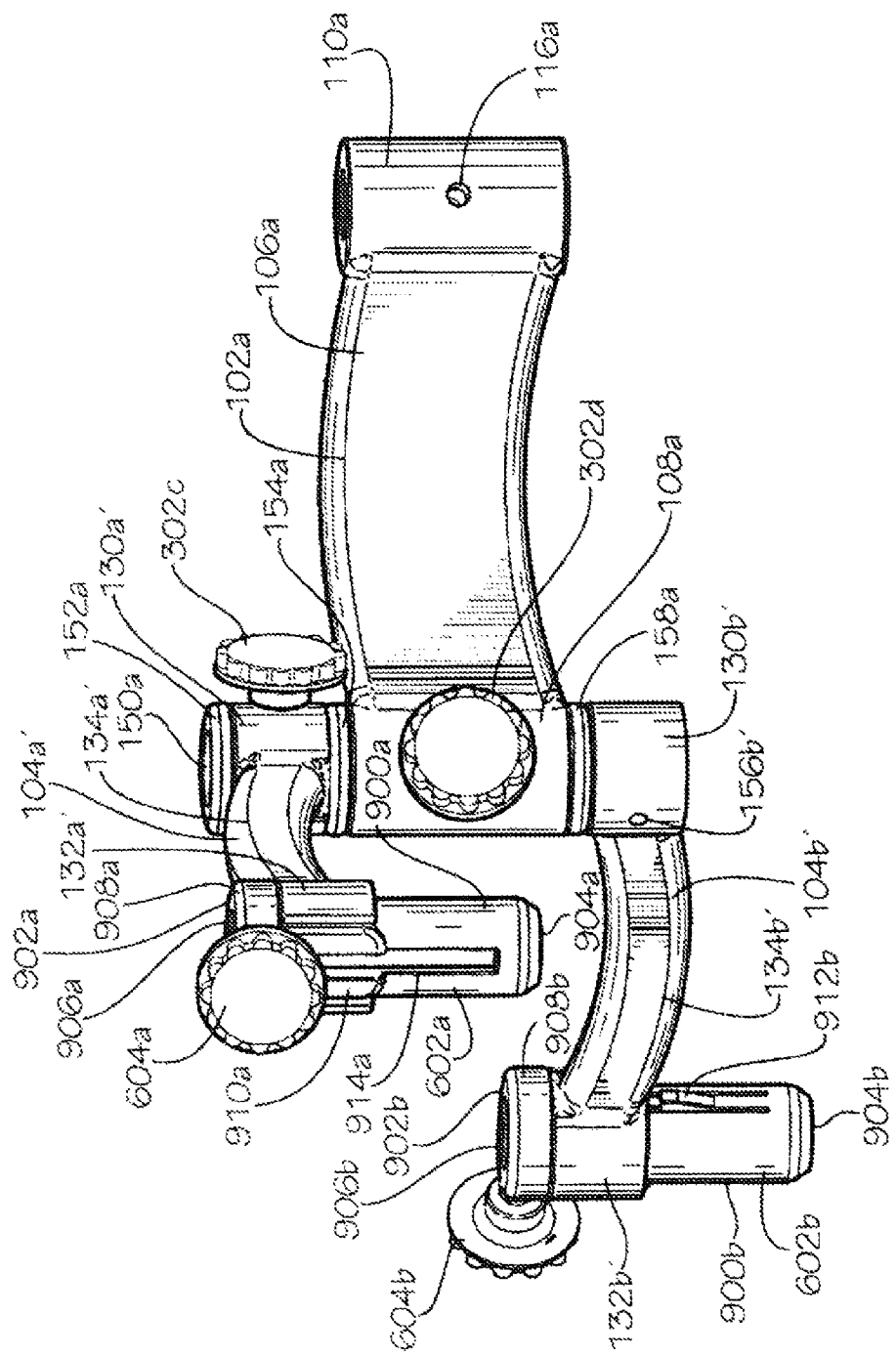
FIG. 9 is a perspective view of a joint connecting the pair of split arms of FIG. 6 and the support arm of FIG. 1.

FIGS. 9 and 10 show the joint where the split arms 104a',b' and the support arm 102a connect. The joint is a pin joint in various embodiments and includes the rod 150a and the collar 152a. Each split arm 104a',b' includes a third connector hub 130a',b' having a top end 136a',b' and a bottom end 138a',b', respectively. In various embodiments, each third connector hub 130a',b' defines the third hub opening 1000a,b extending through each third connector hub 130a',b' from the top end 136a',b' to the bottom end 138a',b', respectively. In various embodiments, each third connector hub 130a',b' defines a third pin opening 156a',b' extending transversely through each third connector hub 130a',b'.

As shown in FIG. 10, the rod 150a is similar to the rod 150g and includes a top end 1002 and a bottom end 1004. In various embodiments, the rod 150a defines a flange 1006 at the top end 1002. The flange 1006 may be utilized to engage the collar 152a and retain the rod 150a in the third hub openings 1000a,b and first hub opening 800a when inserted into the third connector hubs 130a',b' and first connector hub 108a. As shown in FIG. 10, in various embodiments, the rod 150a defines the rod opening 1008 extending transversely through the rod 150a. In various embodiments, the rod opening 1008 may extend transversely through a part of the rod 150a or through the entire rod 150a. The rod opening 1008 is dimensioned to accept the second securing pin 1010. In various embodiments, the rod 150a defines a rod length from the top end 1002 to the bottom end 1004. The length of the rod 150a should not be considered limiting as the rod 150a may have any desired length to accommodate any number of support arms 102a, split arms 104', and mounting arms 200 at the joint.

In various embodiments, the rod opening 1008 is defined on the rod 150a proximate to the bottom end 1004 such that when the rod 150a is inserted into the hub openings to be joined, such as the first hub opening 800a and third hub openings 1000a,b, the second securing pin 1010 may be inserted into the pin opening, such as the third pin opening 156b', of the lowermost arm on the rod 150a, such as split arm 104b', and into the rod opening 1008.

As shown in FIG. 10, the collar 152a is annular in various embodiments and defines a collar opening 1012. In various embodiments, the collar opening 1012 is dimensioned to accept the rod 150a through the collar opening 1012 but prevent the flange 1006 from passing through the collar opening 1012.

In various embodiments, the first spacer 154a is annular and defines a first spacer opening 1014 and the second spacer 158a is annular and defines a second spacer opening 1016. In various embodiments, the collar 152a, the first spacer 154a, and the second spacer 158a may all be the same structure or constructed similarly. The spacer openings 1014,1016 are dimensioned to accept the rod 150a through the spacer openings 1014,1016. In various embodiments, the spacer openings 1014,1016 are dimensioned to prevent the flange 1006 from passing through the spacer openings 1014,1016. The number of spacers 154a,158a should not be considered limiting on the current disclosure as in various other embodiments, the support arm assembly 600 may include any desired number of spacers 154a,158a, including no spacers. Additionally, the location of the spacers 154a, 158a on the rod 150a should not be considered limiting on the current disclosure. When assembled, the collar opening 1012, third hub openings 1000a,b, first spacer opening 1014, and second spacer opening 1016 are aligned and accept the rod 150a through the respective openings.

The second securing pin 1010 is inserted through the third pin opening 156b' and into the rod opening 1008 such that the second securing pin 1010 is positioned in both the third pin opening 156b' and the rod opening 1008. In this manner, the rod 150a is secured in the joint through the securing pin 1010 and the flange 1006 interacting with the collar 152a.

As shown in FIG. 10, each securing knob 302c,d includes a knob pin 814c,d. In various embodiments, the knob pin 814c includes threading to engage the first pin opening 114a. The knob pin 814c is positioned in the first pin opening 114a and engages the first pin opening 114a. The knob pin 814c and may be selectively tightened via the knob 302c to engage the rod 150a. Engagement of the knob pin 814c with the rod 150a may secure the support arm 102a in place on the rod 150a. In various embodiments, the knob pin 814d is positioned in the third pin opening 156a' and may be selectively tightened via the knob 302d to engage the rod 150a. Engagement of the knob pin 814d with the rod 150a may secure the split arm 104a' in place on the rod 150a.

Each split arm 104a',b' includes a split arm body 134a',b', the third connector hub 130a',b', and the support hub 132a', b'. As shown in FIG. 10, each support hub 132a',b' includes a top end 140a',b' and a bottom end 142a',b'. In various embodiments, each support hub 132a',b' defines a support opening 144a',b' extending through the support hub 132a',b' from the top end 140a',b' to the bottom end 142a',b'. In various embodiments, each support hub 132a',b' defines an engagement slot 1018a,b. In various embodiments, each engagement slot 1018a,b extends from the top end 140a',b' to the bottom end 142a',b', respectively. In various other embodiments, each engagement slot 1018a,b is defined in each support hub 132a',b' for a distance less than a distance from the top end 140a',b' to the bottom end 142a',b', respectively.

In various embodiments, each support hub 132a',b' includes the support opening 144a',b' and engagement slot 1018a,b dimensioned to accept alignment ridges 910a,b of the plugs 602a,b, respectively, as described in greater detail below. Each plug 602a,b includes a plug body 900a,b having a top end 902a,b and a bottom end 904a,b, respectively. The plugs 602a,b have a generally cylindrical shape; however the shape should not be considered limiting as in various other embodiments, the plugs 602a,b may have any desired shape. In various embodiments, each plug 602a,b defines a plug opening 906a,b extending from the top end 902a,b to the bottom end 904a,b, respectively.

Figure 14:
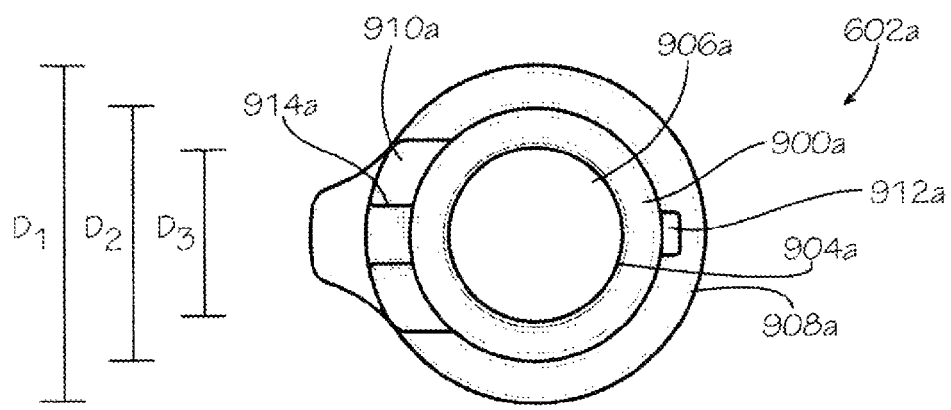
FIG. 14 is a bottom view of the plug of FIG. 11.

In various embodiments, each plug 602a,b includes a plug collar 908a,b at the top end 902a,b, respectively. Each plug collar 908a,b includes collar surfaces 1100a (shown in FIG. 11) (plug surface for plug collar 908b not shown). In various embodiments, as shown in FIG. 14, a diameter of the plugs 602a,b at the plug collar 908a,b is greater than a diameter of the plug body 900a,b between the top end 902a,b and the bottom end 904a,b, which is greater than a diameter of the plug body 900a,b at the bottom end 904a,b. In various embodiments, the diameter of the plugs 602a,b at the plug collar 908a,b is greater than a diameter of the support openings 144a',b'. In various embodiments, the diameter of the plug body 900a,b between the top end 902a,b and the bottom end 904a,b is less than the diameter of the support openings 144a',b'. In various embodiments, the diameter of the plug body 900a,b at the bottom end 904a,b is less than the diameter of the support openings 144a',b'.

The plugs 602a,b may also include alignment ridges 910a,b, respectively. In various embodiments, the alignment ridge 910a is dimensioned to fit in the engagement slots 1018a,b (shown in FIG. 10) of the support hubs 132a',b' and keep the plugs 602a,b oriented in a particular direction relative to the split arms 104a',b' and thereby prevent the plugs 602a,b from rotating within the support hubs 132a',b'.

In various embodiments, each plug 602a,b includes a latch 912a,b (912a shown in FIG. 11), respectively. The latches 912a,b may secure the plugs 602a,b within the support hubs 132a',b' and prevent accidental removal of the plugs 602a,b from the support hubs 132a',b'. The plugs 602a,b may also include lateral slots 914a (lateral slot in plug 602b not shown). In various embodiments, the lateral slot 914a may be defined in the plug body 900a for a distance less than a distance between the top end 902a and the bottom end 904a. The lateral slot 914a may be utilized to form the latch 912a in various embodiments during manufacture. In various other embodiments, the lateral slot 914a is omitted from the plug 602a.

Each plug 602a,b may also define plug pin openings 1028a (shown in FIG. 10) (plug pin opening of plug 602b not shown). The plug pin opening 1028a may extend transversely through the plug 602a. In various embodiments, the plug pin opening 1028a may extend transversely through a part of the plug 602a or through the entire plug 602a.

Each securing knob 604a,b includes a knob pin 1030a,b. In various embodiments, the knob pins 1030a,b may having threading to engage the plug pin openings. In various embodiments, each knob pin 1030a,b is positioned in the plug pin openings, such as plug pin opening 1028a, and may be selectively tightened via the knobs 604a,b to engage a piece of medical equipment, such as IV poles 304a,b, inserted into the plug openings 906a,b. Engagement of the knob pin 1030a,b with the IV poles 304a,b may secure the plugs 602a,b at a desired position along a length of the IV poles 304a,b to allow the IV poles 304a,b to be placed at various desired heights on the support arm assembly 600.

FIGS. 11-14 show the plug 602a in greater detail. Although reference is made to plug 602a in these figures, the below discussion is equally applicable to plug 602b, which is structurally similar to plug 602a in the current embodiment. The plug 602a includes the body 900a having the top end 902a and the bottom end 904a. In various embodiments, the body 900a defines the plug opening 906a extending through the body 900a from the top end 902a to the bottom end 904a.

Figure 11:
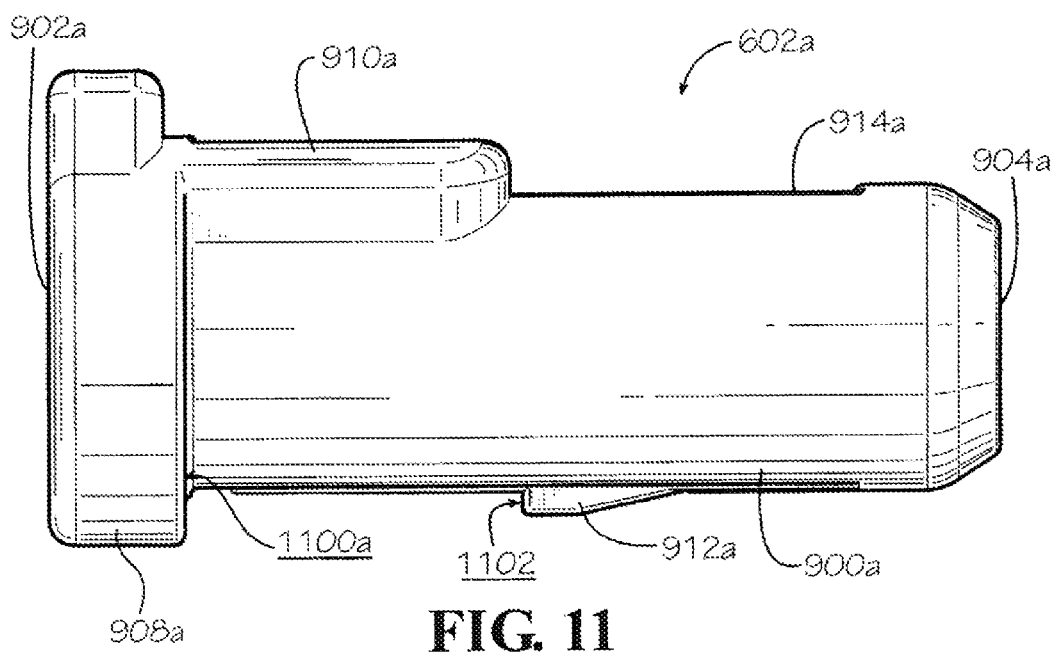
FIG. 11 is a side view of a plug.
Figure 12:
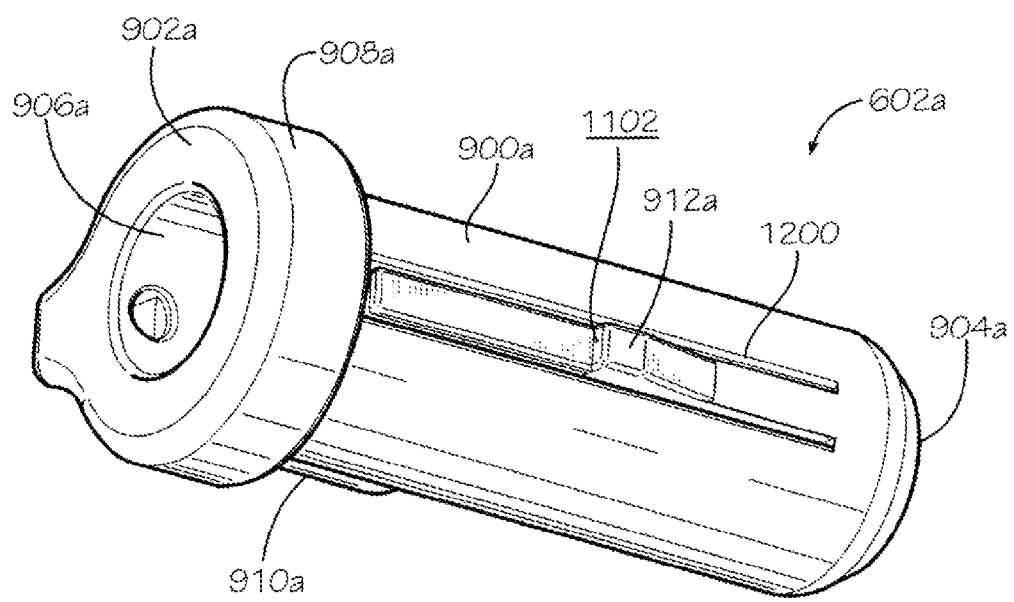
FIG. 12 is a perspective view of the plug of FIG. 11.

As shown in FIG. 11, the plug 602a includes the plug collar 908a at the top end 902a in various embodiments. The plug collar 908a defines the collar surface 1100a. In various embodiments, when the plug 602a is positioned in the support hub 132a', the collar surface 1100a faces the top end 140a' of the support hub 132a'. The collar surface 1100a may contact the top end 140a' of the support hub 132a' in various embodiments. The plug 602a also includes the alignment ridge 910a in various embodiments. The plug 602a may also include the securing latch 912a. The securing latch 912a may include a latch surface 1102. In various embodiments, when the plug 602a is positioned in the support hub 132a', the latch surface 1102 faces the bottom end 142a' of the support hub 132a'. In various embodiments, the latch surface 1102 faces the collar surface 1100a. In various embodiments, a distance from the latch surface 1102 to the collar surface 1100a is greater than a distance from the top end 140a' to the bottom end 142a' of the support hub 132a'. In various embodiments, the distance from the latch surface 1102 to the collar surface 1100a is slightly greater than the distance from the top end 140a' to the bottom end 142a' of the support hub 132a' such that when the plug 602a is positioned in the support hub 132a', a tight fit is formed between the collar surface 1100a and the top end 140a' and between the latch surface 1102 and the bottom end 142a'. In this manner, the plug 602a may be held securely in place on the support hub 132a'.

As shown in FIG. 11, in various embodiments, the securing latch 912a is integrally formed with the plug body 900a. In various embodiments, the plug body 900a defines a latch slot 1200 around the latch 912a. In various embodiments, the latch 912a is depressible into the latch slot 1200. In various embodiments, when the latch 912a is not depressed into the latch slot 1200, the latch 912a extends radially outwards from the plug body 900a. When the plug 602a is positioned on the support hub 132a', the latch 912a may not be depressed into the latch slot 1200 and the latch surface 1102 engages the bottom end 142a'. In various embodiments, to disengage the plug 602a from the support hub 132a', the latch 912a is depressed into the latch slot 1200 such that the plug 602a may be removed from the support hub 132a'. The shape or location of the latch 912a should not be considered limiting on the current disclosure as in various other embodiments, the latch 912a may have any desired shape or positioned at any desired location on the plug 602a. In various embodiments, the latch 912a may be integrally formed with the body 900a or may be connected to the body 900a with a connection mechanism such as a snap, screw, tab, nut, bolt, or other similar connection mechanism.

Figure 13:
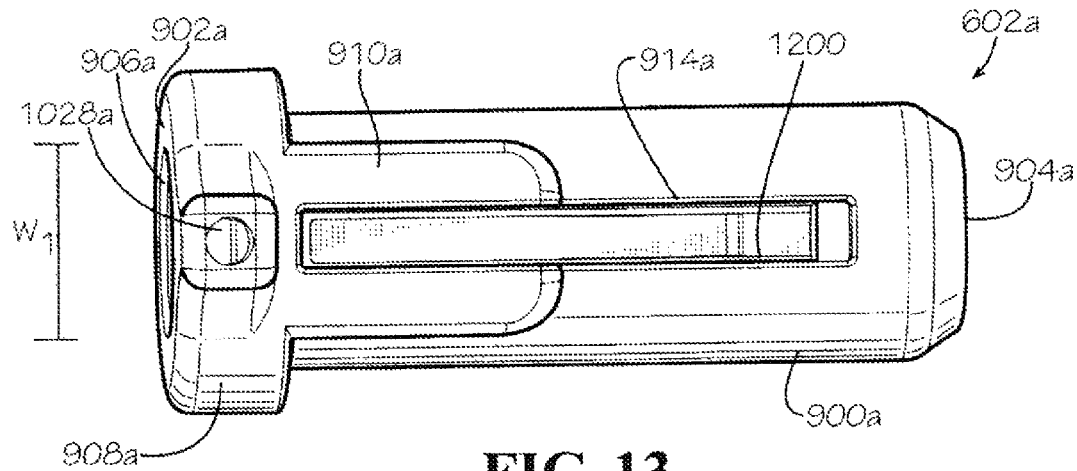
FIG. 13 is another side view of the plug of FIG. 11.

FIG. 13 shows the plug pin opening 1028a defined in the plug body 900a. In various embodiments, the plug pin opening 1028a is defined transversely through the plug body 900a proximate to the top end 902a. In various embodiments, the plug pin opening 1028a is defined through the plug collar 908a. In various other embodiments, the plug pin opening 1028a may be defined at any desired location on the plug body 900a.

The plug 602a may also include the lateral slot 914a. In various embodiments, the lateral slot 914a may be defined in the plug body 900a for a distance less than a distance between the top end 902a and the bottom end 904a. In various embodiments, the lateral slot 914a is defined through the alignment ridge 910a. As shown in FIG. 13, in various embodiments, the lateral slot 914a may be defined in the plug body 900a at a position opposite the latch slot 1200 such that the lateral slot 914a and latch slot 1200 are aligned. In various embodiments, the alignment ridge 910a has a first width $W_1$.

FIG. 14 shows a bottom view of the plug 602a. As shown in FIG. 14, in various embodiments, the plug collar 908a defines a first diameter $D_1$, the body 900a between the top end 902a and the bottom end 904a defines a second diameter $D_2$, and the bottom end 904a defines a third diameter $D_3$. In various embodiments, the first diameter $D_1$ is greater than the second diameter $D_2$ and the third diameter $D_3$. In various embodiments, the second diameter $D_2$ is greater than the third diameter $D_3$. In various embodiments, the second diameter $D_2$ is less than the diameter of the support opening 144a' and greater than a diameter of the IV pole 304a. In various embodiments, the third diameter $D_3$ is less than the diameter of the support opening 144a' and greater than a diameter of the IV pole 304a. The third diameter $D_3$ is less than the diameter of the support opening 144a' and greater than a diameter of the IV pole 304a and may help to guide the plug 602a into the support hub 132a'.

Figure 15:
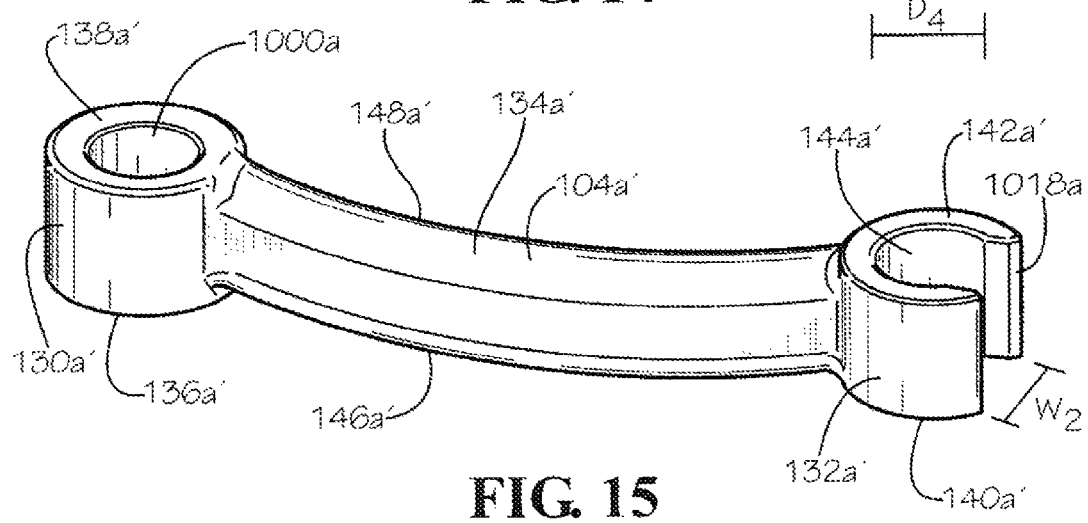
FIG. 15 is a perspective view of a one of the pair of split arms of FIG. 6.

FIG. 15 shows the split arm 104a'. Although reference is now made to split arm 104a', the below discussion is equally applicable to split arm 104b', which is structurally similar to split arm 104a' in the current embodiment. As shown in FIG. 15, the split arm 104a' includes the split arm body 134a', the third connector hub 130a', and the support hub 132a'. In various embodiments, the third connector hub 130a' includes a top end 136a', a bottom end 138a', and a third hub opening 1000a extending from the top end 136a' to the bottom end 138a'.

In various embodiments, the split arm body 134a' includes a top end 146a' and a bottom end 148a'. A profile of the top end 146a' may be concave between the third connector hub 130a' and the support hub 132a' and a profile of the bottom end 148a' may be convex between the third connector hub 130a' and the support hub 132a'. However, the shape of the split arm body 134a' should not be considered limiting on the current disclosure as in various other embodiments, the split arm body 134a' may be rectangular, angled, or have any other desired shape.

The support hub 132a' includes a top end 140a' and a bottom end 142a'. The support hub 132a' defines the support opening 144a' through the support hub 132a' from the top end 140a' to the bottom end 142a'. As shown in FIG. 15, the support opening 144a' has a fourth diameter $D_4$. In various embodiments, the fourth diameter $D_4$ is greater than the second diameter $D_2$ of the plug 602a and less than the first diameter $D_1$ of the plug 602a.

The support hub 132a' also defines the engagement slot 1018a. In various embodiments, the engagement slot 1018a extends from the top end 140a' to the bottom end 142a'. In various other embodiments, the engagement slot 1018a is defined in the support hub 132a' for a distance less than a distance from the top end 140a' to the bottom end 142a'. As shown in FIG. 15, the engagement slot 1018a has a second width $W_2$. In various embodiments, the second width $W_2$ is greater than the first width $W_1$ of the alignment ridge 910a. In various embodiments when the plug 602a is positioned in the support hub 132a', the alignment ridge 910a is positioned in the engagement slot 1018a. In various embodiments, the second width $W_2$ is less than the second diameter $D_2$ of the plug 602a.

Figure 16:
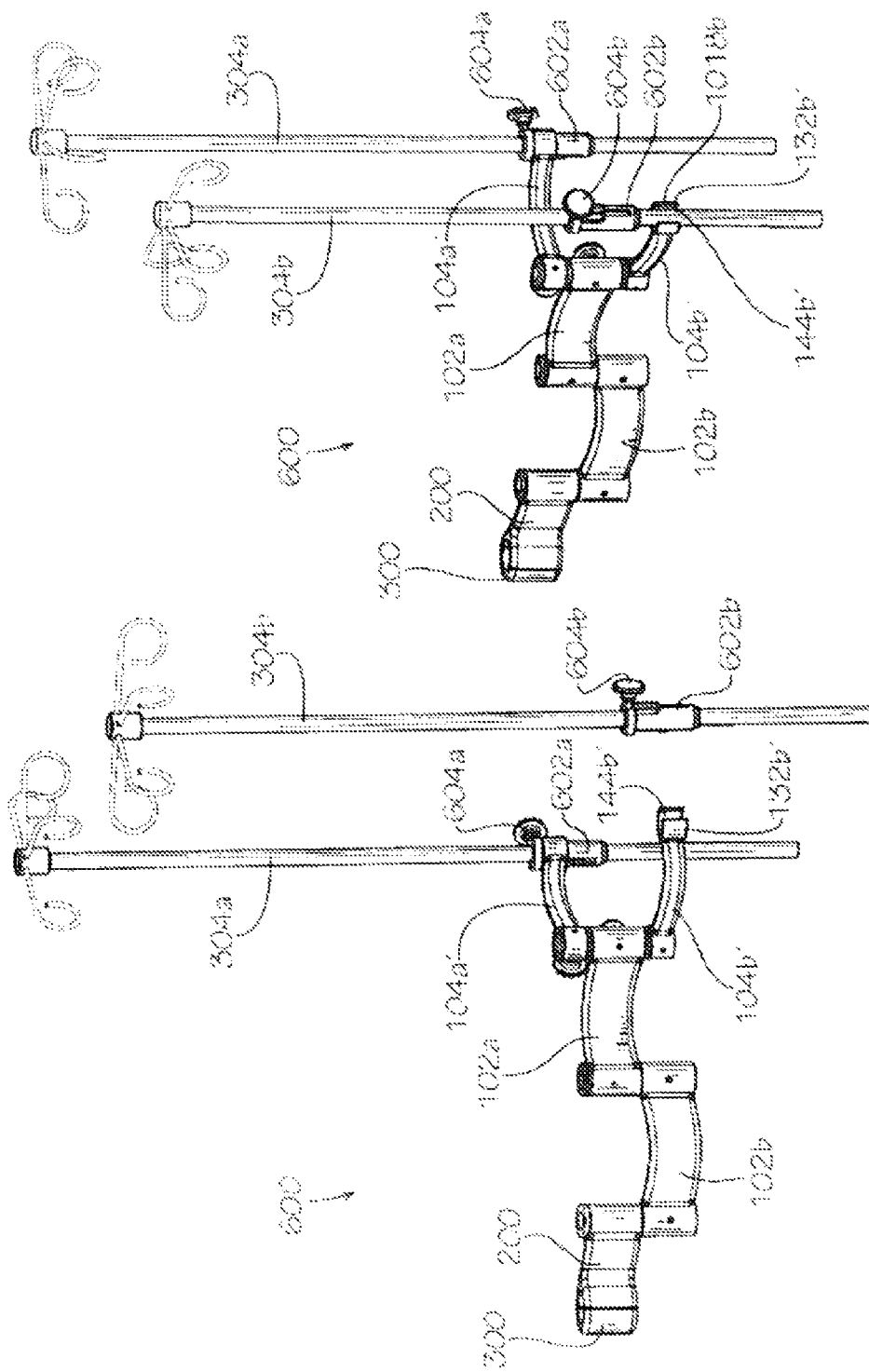
FIG. 16A is a perspective view of the plug of FIG. 11 on an IV post before mounting of the plug on the support arm assembly of FIG. 6.
FIG. 16B is a perspective view of the plug of FIG. 11 on an IV post during mounting of the plug on the support arm assembly of FIG. 6.
FIG. 16C is a perspective view of the plug of FIG. 11 on an IV post after mounting of the plug on the support arm assembly of FIG. 6.

A method of positioning a piece of medical equipment, such as the IV poles 304a,b, in the support arm assembly 600 is also disclosed. As shown in FIG. 16A, the plug 602b is positioned in the IV pole 304b by inserting the IV pole 304b through the plug opening 906b (shown in FIG. 10). The plug 602b is positioned at a desired location along the IV pole 304b and the securing knob 604b is tightened such that the knob pin 1030b (shown in FIG. 10) engages the IV pole 304b and secures the plug 602b on the IV pole 304b.

As shown in FIG. 16B, the IV pole 304b with plug 602b is positioned such that the IV pole 304b extends through the support opening 144b' of the support hub 132b' of the split arm 104b' and the plug 602b is positioned above the support hub 132b'. As shown in FIG. 16C, the IV pole 304b with the plug 602b is slid downwards through the support opening 144b' such that the plug body 900b is positioned in the support opening 144b'. In various embodiments, the collar surface 1100a (shown in FIG. 11) of the plug collar 908b contacts an end of the support hub 132', such as the top end 140b'. The latch surface 1102 of the latch 912b (shown in FIG. 11) contacts another end of the support hub 132', such as the bottom end 142b'.

The alignment ridge 910b is positioned in the engagement slot 1018b of the support hub 132b'. The split arm 104b' may be movably positioned relative to the split arm 104a' and the support arm 102a to position the IV pole 304b as desired. The support arm 102a may also be movably positioned relative to the support arm 102b and the support arm 102b may also be movably positioned relative to the mounting arm 200 to further position the IV pole 304b at a desired location.

Figure 17:
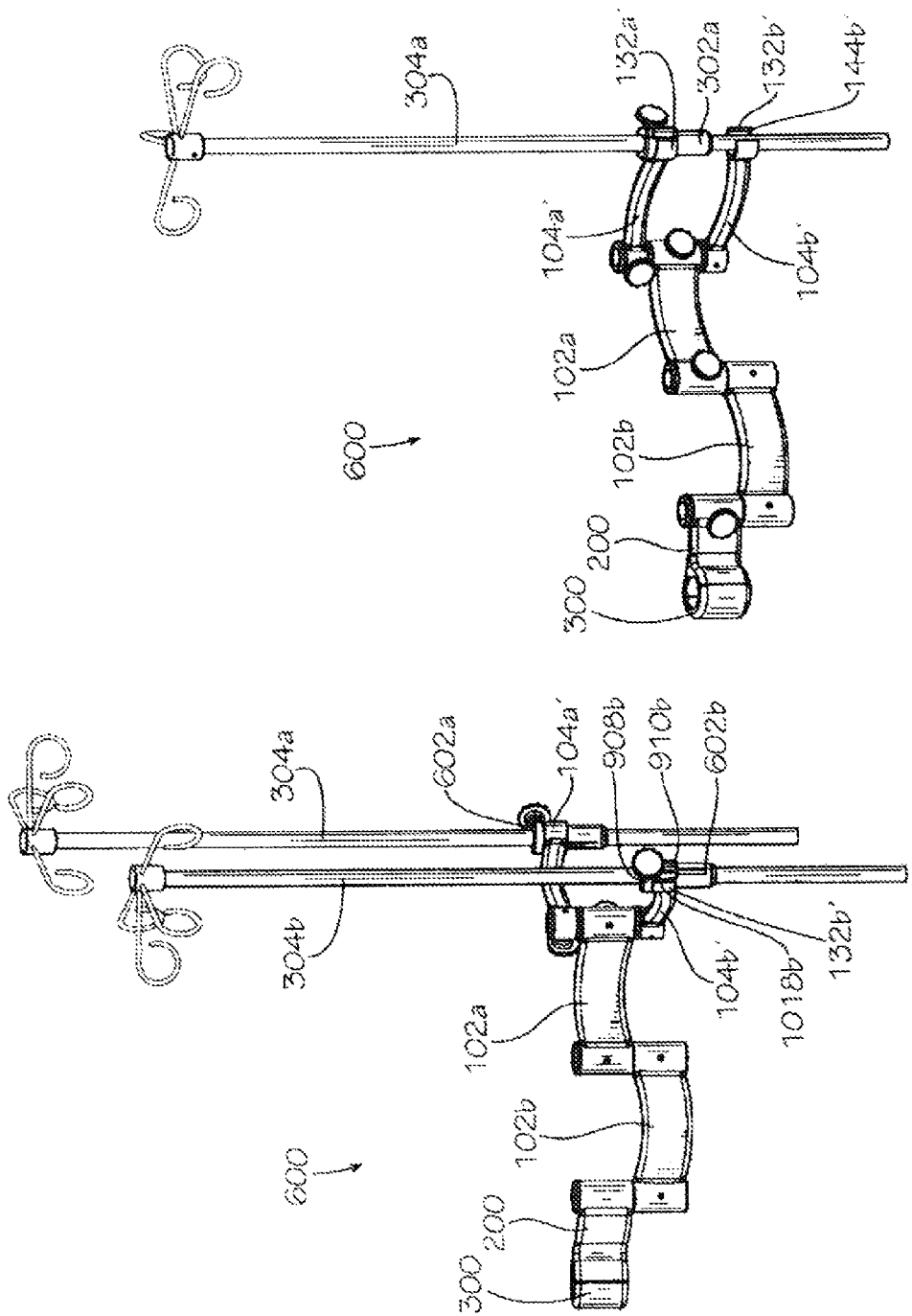
FIG. 17 is a perspective view of the support arm assembly of FIG. 6 with two support arms supporting a single IV post.

FIG. 17 shows a configuration of the support arm assembly 600 with the IV pole 304a supported by both split arms 104a',b'. As shown in FIG. 17, in this configuration, the plug 602a positioned on the IV pole 304a is positioned in the support opening 144a' of the support hub 132a' and a portion of the IV pole 304a below the plug 602a is positioned in the support opening 144b' of the support hub 132b' to prevent movement of the split arm 104b' when it is not in use supporting other medical equipment. However, this configuration should not be considered limiting on the current disclosure as in various other embodiments, the plug 602a may be positioned in the support opening 144b' of the support hub 132b' and a portion of the IV pole 304a above the plug 602a may be positioned in the support opening 144a' of the support hub 132a'. In various other embodiments, the IV pole 304a may include two plugs, such as plugs 602a,b positioned on the IV pole 304a with the respective plugs 602a,b positioned in the respective support openings 144a',b' of the support hubs 132a',b'. The number of plugs 602a,b or split arms 104a',b' engaging the plugs 602a,b on the IV pole 304a should not be considered limiting on the current disclosure as in various other embodiments, any desired number of plugs 602a,b and split arms 104a',b' may be utilized.

Figure 18:
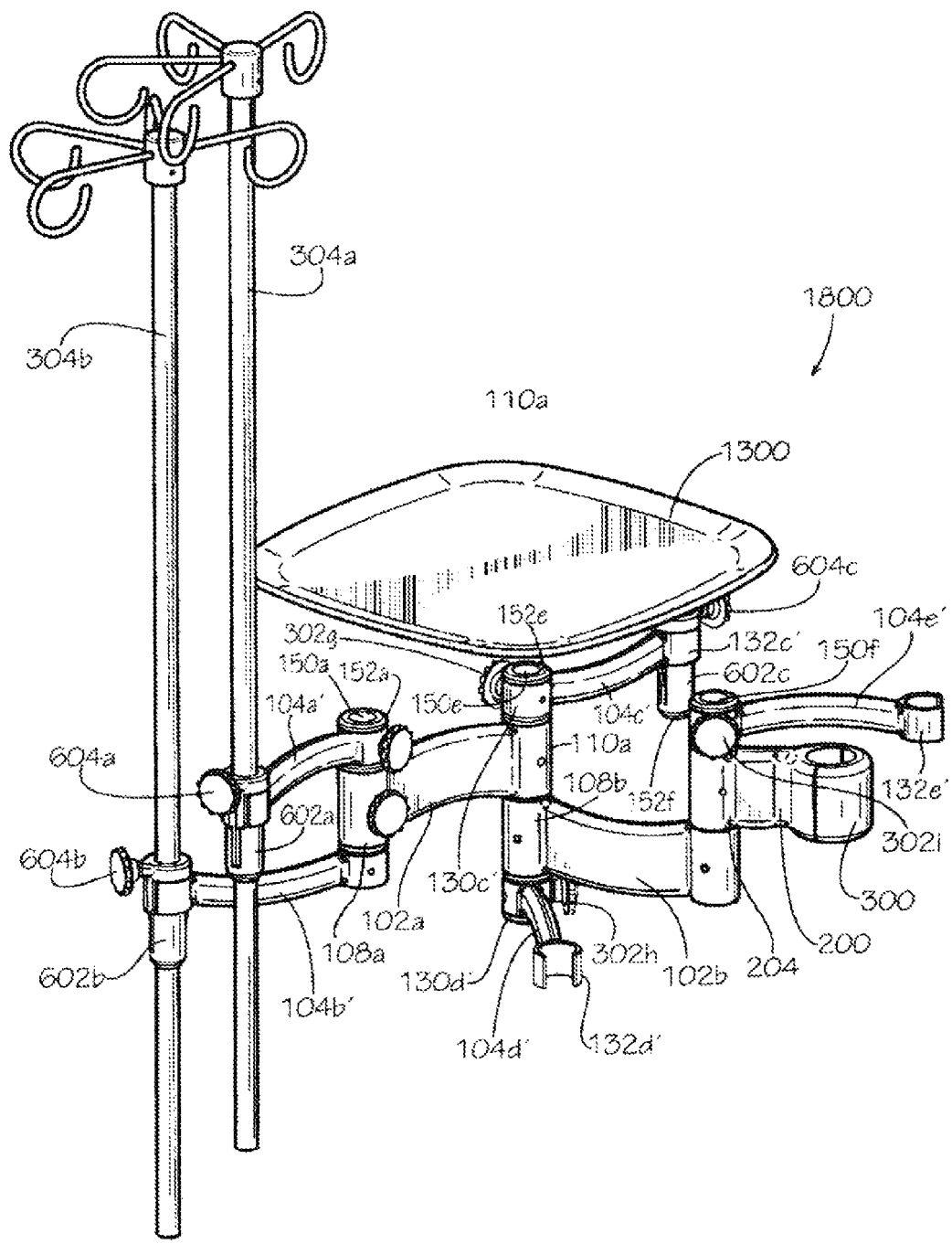
FIG. 18 is another embodiment of a support arm assembly with the mounting arm and pair of support arms shown in FIG. 3 and five split arms as shown in FIG. 15.

FIG. 18 shows another embodiment of a support arm assembly 1800. As shown in FIG. 18, the support arm assembly 1800 includes split arms 104c',d',e' in addition to split arms 104a',b'. In the present embodiment, split arms 104b',c' are in an upside-down orientation compared to the orientation of split arm 104a' in FIG. 6. Split arms 104a',d',e' are in the same orientation as the orientation of split arm 104a' in FIG. 6. As shown in FIG. 18, in various embodiments, the split arms 104c',d',e' may include securing knobs 302g,h,i. As shown in FIG. 18, the split arms 104c',d' are included at the joint where the support arm 102a and the support arm 102b connect. In various embodiments, the split arm 104c' is positioned above the second connector hub 110a of the support arm 102a and the split arm 104d' is positioned below the first connector hub 108b of the support arm 102b. In various embodiments, a length of a rod 150e where the split arms 104c',d' and support arms 102a,b are connected is greater than the length of the rod 150a. As shown in FIG. 13, in various embodiments, the support arm assembly 1800 may support medical equipment other than the IV poles 304a,b. In the present embodiment, the support arm assembly 1800 also supports a medical tray 1300 through the split arm 104c'. In various embodiments, the medical tray 1300 may include a connecting mechanism which may engage a support hub 132d of the split arm 104c' directly or may engage the support hub 132c' through a plug 602c having a securing knob 604c.

As shown in FIG. 18, the split arm 104e' is included at the joint where the support arm 102b and the mounting arm 200 connect. In various embodiments, the split arm 104e' is positioned above the mounting hub 204 of the mounting arm 200. A length of a rod 150f of this joint may be greater than the length of the rod 150a.

The configurations of the support arm assembly 100, the support arm assembly 500, the support arm assembly 600, or support arm assembly 1800 should not be considered limiting on the current disclosure. In various embodiments, a single joint, or the location where at least two arms are connected, may include any desired number of arms, such as the split arms 104a,b,a',b', the support arms 102a,b,c, or the mounting arm 200. The split arms 104a,b,a',b' may be utilized to support any desired piece of medical equipment, such as the IV poles 304a,b or medical tray 1300, either with the use of plugs, such as plugs 602a,b,c, or without utilizing plugs.

One should note that conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more particular embodiments or that one or more particular embodiments necessarily include logic for deciding, with or without user input or prompting, whether these features, elements and/or steps are included or are to be performed in any particular embodiment.

It should be emphasized that the above-described embodiments are merely possible examples of implementations, merely set forth for a clear understanding of the principles of the present disclosure. Many variations and modifications may be made to the above-described embodiment(s) without departing substantially from the spirit and principles of the present disclosure. Further, the scope of the present disclosure is intended to cover any and all combinations and sub-combinations of all elements, features, and aspects discussed above. All such modifications and variations are intended to be included herein within the scope of the present disclosure, and all possible claims to individual aspects or combinations of elements or steps are intended to be supported by the present disclosure.

That which is claimed is:

1. A support arm assembly comprising:
a support arm, the support arm including a support arm connector hub and a support arm body;
a split arm, the split arm including a split arm connector hub and a support hub, the split arm connector hub connected to the support arm connector hub, the support hub comprising a top end, a bottom end distal from the top end, and a side wall defining a side wall surface and extending from the top end to the bottom end, the support hub defining a support bore extending through the support hub from the top end to the bottom end and an engagement slot extending transversely through the side wall from the side wall surface to the support bore; and
a plug comprising a body having top end, a bottom end distal from the top end, and a side wall extending from the top end to the bottom end, the plug defining a plug collar at the top end, the plug collar defining a collar surface, the plug collar defining an outer diameter which is greater than a diameter of the support bore, the plug configured for reception of the body of the plug within the support bore of the split arm and for engagement of the collar surface with the top end of the support hub.

2. The support arm assembly of claim 1, wherein the split arm is connected to the support arm through a joint rod, the joint rod extending through the support arm connector hub and the split arm connector hub, and wherein the split arm is rotatable on the joint rod relative to the support arm.

3. The support arm assembly of claim 1, wherein the support arm is a first support arm, the assembly further comprising a second support arm having a second support arm connector hub connected to the support arm connector hub.

4. The support arm assembly of claim 1,
wherein the plug defines a plug bore extending through the plug from the top end to the bottom end,
wherein the plug defines an alignment ridge extending outwards from the side wall of the plug, and
wherein the alignment ridge is configured for reception within the engagement slot of the support hub.

5. The support arm assembly of claim 1, wherein the plug further comprises:
a latch, the latch defining a latch surface, the latch surface and the collar surface facing each other, wherein a distance from the latch surface to the collar surface is greater than a distance from the top end of the support hub to the bottom end of the support hub.

6. The support arm assembly of claim 1, wherein:
the support arm connector hub includes a top end and a bottom end;
the support arm connector hub defines a support arm hub bore extending through the support arm connector hub from the top end to the bottom end;
the support arm connector hub defines a first pin opening extending transversely through the support arm connector hub;
the split arm connector hub includes a top end and a bottom end;
the split arm connector hub defines a split arm hub opening extending through the split arm connector hub from the top end to the bottom end; and
the split arm connector hub defines a second pin opening extending transversely through the split arm connector hub.

7. The support arm assembly of claim 6, further comprising:
a joint rod insertable through the split arm hub opening and the support arm hub opening, wherein the joint rod defines a rod opening; and
a securing pin insertable through a one of the first pin opening or the second pin opening and into the rod opening.

8. The support arm assembly of claim 7, further comprising a securing knob, the securing knob including an engagement pin insertable into a second of the first pin opening or the second pin opening.

9. The support arm assembly of claim 1, further comprising a mounting arm, wherein the mounting arm includes a mounting hub and a mounting mechanism, wherein the support arm connector hub is a first support arm connector hub and the support arm includes a second support arm connector hub, and wherein the mounting hub is connected to one of the first support arm connector hub or the second support arm connector hub.

10. The support arm assembly of claim 1, wherein the support arm connector hub is a first support arm connector hub and the support arm includes a second support arm connector hub, and wherein the support arm is a first support arm, the assembly further comprising:
a second support arm connected to the second support arm connector hub; and
a third support arm connected to the second support arm connector hub.

11. The support arm assembly of claim 1, wherein the split arm is a first split arm, the split arm connector hub is a first split arm connector hub, and the support hub is a first support hub, and wherein the first split arm contacts a top end of the support arm connector hub, the assembly further comprising:
a second split arm, the second split arm including a second split arm connector hub and a second support hub, the second split arm connector hub connecting to the support arm connector hub and contacting a bottom end of the support arm connector hub.

12. The support arm assembly of claim 11, wherein the first support hub of the first split arm and the second support hub of the second split arm support a single item.

13. The support arm assembly of claim 11, wherein the first support hub of the first split arm supports a first item and the second support hub of the second split arm supports a second item.

14. The support arm assembly of claim 1, wherein the body of the plug defines a second diameter between the plug collar and the bottom end, and wherein the body of the plug defines a third diameter at the bottom end, and wherein the second diameter is greater than the third diameter and less than the outer diameter of the plug collar.

15. The support arm assembly of claim 1, wherein the plug defines a pin bore extending transversely through the plug collar, the pin bore configured for receiving a securing pin through the pin bore.

16. A method comprising:
connecting a split arm connector hub of a split arm to a support arm connector hub of a support arm;
mounting the support arm on a structure;
positioning a body of a plug within a support bore of the split arm and engaging a collar surface of a plug collar of the plug with a top end of a support hub of the split arm, the support bore defined through the support hub of the split arm and extending from the top end to a bottom end of the support hub;
positioning an alignment ridge of the plug in an engagement slot of the support hub, the engagement slot extending transversely through a side wall of the support hub from a side wall surface of the side wall to the support bore and from the top end of the support hub to the bottom end of the support hub;
supporting an item through the plug; and
moving the split arm relative to the support arm.

17. The method of claim 16, wherein mounting the support arm on the structure includes mounting a mounting mechanism of a mounting arm on the structure, and connecting a mounting hub of the mounting arm to a support arm hub of the support arm.

18. The method of claim 16, further comprising securing the split arm at a position relative to the support arm.

19. A support arm assembly comprising:
a support arm, the support arm including a support arm connector hub and a support arm body;
a split arm, the split arm including a split arm connector hub and a support hub, the split arm connector hub connected to the support arm connector hub, the support hub comprising a top end, a bottom end distal from the top end, and a side wall defining a side wall surface and extending from the top end to the bottom end, the support hub defining a support bore extending through the support hub from the top end to the bottom end and an engagement slot extending transversely through the side wall from the side wall surface to the support bore; and
a plug comprising a body having top end, a bottom end distal from the top end, and a side wall extending from the top end to the bottom end, the plug defining an alignment ridge extending outwards from the side wall of the plug, the alignment ridge configured for reception within the engagement slot of the support hub, the plug defining a plug bore extending through the plug from the top end to the bottom end, the plug defining a plug collar at the top end, the plug collar defining a collar surface, the plug configured for reception of the body of the plug within the support bore of the split arm and for engagement of the collar surface with the top end of the support hub.

20. The support arm assembly of claim 19, wherein the plug further comprises:
a latch, the latch defining a latch surface, the latch surface and the collar surface facing each other, wherein a distance from the latch surface to the collar surface is greater than a distance from the top end of the support hub to the bottom end of the support hub.

21. The support arm assembly of claim 19, wherein the split arm is connected to the support arm through a joint rod, the joint rod extending through the support arm connector hub and the split arm connector hub, and wherein the split arm is rotatable on the joint rod relative to the support arm.

22. The support arm assembly of claim 19, wherein the plug defines a pin bore extending transversely through the plug collar, the pin bore configured for receiving a securing pin through the pin bore.

23. The support arm assembly of claim 19, further comprising a mounting arm, wherein the mounting arm includes a mounting hub and a mounting mechanism, wherein the support arm connector hub is a first support arm connector hub and the support arm includes a second support arm connector hub, and wherein the mounting hub is connected to one of the first support arm connector hub or the second support arm connector hub.

24. The support arm assembly of claim 19, wherein:
the support arm connector hub includes a top end and a bottom end;
the support arm connector hub defines a support arm hub bore extending through the support arm connector hub from the top end to the bottom end;
the support arm connector hub defines a first pin opening extending transversely through the support arm connector hub;
the split arm connector hub includes a top end and a bottom end;
the split arm connector hub defines a split arm hub opening extending through the split arm connector hub from the top end to the bottom end; and
the split arm connector hub defines a second pin opening extending transversely through the split arm connector hub.

25. The support arm assembly of claim 24, further comprising:
a joint rod insertable through the split arm hub opening and the support arm hub opening, wherein the joint rod defines a rod opening; and
a securing pin insertable through a one of the first pin opening or the second pin opening and into the rod opening.

\* \* \* \* \*